US006998514B2

(12) United States Patent
Bruggemann

(10) Patent No.: US 6,998,514 B2
(45) Date of Patent: Feb. 14, 2006

(54) MURINE EXPRESSION OF A HUMAN IGA LAMBDA LOCUS

(75) Inventor: Marianne Bruggemann, Cambridge (GB)

(73) Assignee: Babraham Institute, Cambridge (GB)

( * ) Notice: Subject to any disclaimer, the term of this patent is extended or adjusted under 35 U.S.C. 154(b) by 208 days.

(21) Appl. No.: 09/734,613

(22) Filed: Dec. 13, 2000

(65) Prior Publication Data

US 2002/0088016 A1 Jul. 4, 2002

(30) Foreign Application Priority Data

Nov. 3, 1998 (GB) .............................. 9823930
Nov. 3, 1999 (GB) .............................. PCT/GB99/03632

(51) Int. Cl.
*A01K 67/027* (2006.01)
*C12N 15/00* (2006.01)
*C12N 15/63* (2006.01)
*C12N 5/00* (2006.01)

(52) U.S. Cl. ............................ 800/18; 800/21; 800/22; 435/320.1; 435/325

(58) Field of Classification Search ................... 800/18, 800/21, 22; 435/325, 320.1
See application file for complete search history.

(56) References Cited

U.S. PATENT DOCUMENTS 6,162,963 A * 12/2000 Kucherlapati ................ 800/18

FOREIGN PATENT DOCUMENTS

| WO | WO90/04036 | 4/1990 |
|---|---|---|
| WO | WO 92/04443 | 3/1992 |
| WO | WO 93/05165 | 3/1993 |
| WO | WO 92/24884 | 6/1998 |
| WO | WO 98/24884 | 6/1998 |
| WO | WO 98/24893 | 6/1998 |

OTHER PUBLICATIONS

Brüggemann et al., Current Opinion in Biotechnology 8: 455–458 (1997).*
Fishwild et al., Nature Biotechnology 14: 845–851 (1996).*
Friguet et al., Journal of Immunological Methods 77: 305–319 (1985).*
Ignatovich, The Creation of Diversity in the Human Immunoglobulin Vλ Repertoire, A thesis submitted to the Univ. of Cambridge in candidature for the degree of Doctor of Philosophy (Oct. 1997).*
Green et al., Nature Genetics 7: 13–12 (1994).
Popov, A., et al, "Assembly and Extension of Yeast Artificial Chromosomes to Build a Large Locus"; Gene: An International Journal on Genes and Genomes; Oct. 24, 1998; pp. 195–201; vol. 177, No. 1; Elsevier Science Publishers, Great Britain.

Gorman, J. et al.; "The Igx 3' Enhancer Influences the Ratio of Igx Versus Igλ B Lymphocytes"; Immunity; Sep. 1996; pp. 241–252; vol. 5, No. 3; Cell Press.
Popov, A., et al; "A Human Immunoglobulin λ Locus Is Similarly Well Expressed in Mice and Humans"; J. Exp. Med; May 17, 1999; pp. 1811–1820; vol. 189, No. 10; The Rockefeller University Press.
Hood, L. et al; "Light Chain Evolution"; Cold Spring Harbour Symp. Quant. Biol.; 1967; pp. 133–148; vol. 32.
McIntire, K.R. et al; "Mouse Immuglobulin Light Chains: Alteration of κλ Ratio"; Federal Proc.; Mar./Apr. 1970; p. 704; vol. 29; No. 2; Federation of American Societies for Experimental Biology.
Arun, S.S. et al; "Immunohistochemical Examination of Light–Chain Expression (λ/κ Ration) in Canine, Feline, equine, Bovine and Porcine Plasma Cells", J. Vet. Med.; Feb. 1996; pp. 573–576; vol. 43; Blackwell Wissenschafts-Verlag; Berlin, Germany.
Hieter, P. "Human Immunoglobulin κ Light–Chain Genes are Deleted or Rearranged in λ–Producing B Cells"; Nature; Apr. 2, 1981; pp. 368–372; vol. 290; Macmillan Journals Ltd.
Coleclough , C. et al; "Aberrant Rearrangements Contribute Significantly to the Allelic Exclusion of Immunoglobulin Gene Expression"; Nature, Apr. 2, 1981; pp. 372–378; vol. 290; Macmillan Journals Ltd.
Selsing, E. et al; "Immunoglobulin λ genes"; Immuglobulin Genes Second Edition; pp. 193–203; Academic Press; London, England.
Berg, J. et al; "Immunoglobulin λ Gene Rearrangement Can Precede κ Gene Rearrangement"; Developmental Immunology; 1990; pp. 53–57; vol. 1:Harwood Academic Publishers GmgH; Great Britain.
Abken, H. et al; "Re–organization of the Immunoglobulin Kappa Gene on Both Alleles is not an Obligatory Prerequisite for Ig Lambda Gene Expression in Human Cells"; Immunology; Aug. 12, 1991; pp. 709–713; vol. 74.
Takemori, T. et al.; "Lambda Chain Expression at Different Stages of Ontogeny in C57BL/6, BALB/c and SJL Mice"; Eur. J Immunology; 1981; pp. 618–625; vol. 11; Verlag Chemie GmbH, Weinheim, Germany.

(Continued)

Primary Examiner—Anne Marie S. Wehbe
(74) Attorney, Agent, or Firm—Heller Ehrman LLP

(57) ABSTRACT

In humans, approximately 60% of expressed immunoglobulin light chains are of the Kappa type and 40% of the Lambda type. In mice, there is almost no expression from the Lambda locus and over 95% of light chains are of Kappa type. The present invention discloses, among other things, transgenic mice carrying most of the human Ig Lambda light chain locus in their genome. The resulting mice express light chains with Kappa/Lambda ratio similar to the human ratio. Breeding of HuIg Lamda mice to Kappa-deficient mice also is described, as well as the generation of human monoclonal antibodies from transgenic mice with human Ig Lambda locus.

28 Claims, 11 Drawing Sheets

OTHER PUBLICATIONS

McGuire, K. et al; "κ/λ Shifts Do Not Occur During Maturation of Murine B Cells"; The Journal of Immunology; Oct. 4, 1981; pp. 1670–1673; vol. 127, No. 4; The American Association of Immunologists; United States.

Kessler, S. et al; "Surface Membrane κ and λ Light Chain expression on Spleen Cells of Neonatal and Maturing Normal and Immune–Defective CBA/n Mice: The κλ Ratio is Constant"; The Journal of Immunology; Oct. 4, 1981; pp. 1674–1678; vol. 127, No. 4; The American Association of Immunologists; United States.

LeJeune, J.M. et al; "Estimate of the Light Chain Repertoire Size of Fetal and Adult BALB/cJ and CBA/J Mice"; The Journal of Immunology; Aug. 2, 1962; pp. 673–677; vol. 129; No. 2; The American Association of Immunologists; United States.

Rolink, A. et al; "The κ/λ Ratio in Surface Immunoglobulin Molecules on B Lymphocytes Differentiating from $D_hI_h$ Rearranged Murine pre–B Cell Clones in vitro"; Eur. J. Immunol. 1991; pp. 2895–2898; vol. 21; Verlagsgssellschaft mbH; Weinheim, Germany.

Osmond, D. et al; "Murine B Lymphopoiesis; Towards a Unified Model"; Immunology Today; Feb. 1998; pp. 65–68; vol. 19, No. 2; Elsevier Science Ltd.; Great Britain.

Zou et al.; "Gene Targeting in the Igx Locus: Efficient Generation of λ Chain–Expressing B Cells, Independent of Gene Rearrangements in Igx"; The EMBO Journal, 1993; pp. 811–820; vol. 12, No. 3; Oxford University Press.

Arakawa, H. et al; "ReEvaluation of the Probabilities for Productive Rearrangements on the κ and λ Loci"; International Immunology, 1998; pp. 91–99; vol. 8; No. 1; Oxford University Press.

Glozak, M. et al; "The Human λ Immunoglobulin Enhancer Is Controlled by Both Positive Elements and Developmentally Regulated Negative Elements"; Molecular Immunology; 1996; pp. 427–438; vol. 33; No. 4/5; Elsevier Science Ltd.; Great Britain.

Asenbauer, H. et al; "Tissue–Specific Deoxyribonuclease I–Hypersensitive Sites in the Vicinity of the Immunglobulin $C_\lambda$ Cluster of Man"; Eur. J. Immunol. 1996; pp. 142–150; vol. 26; Vertagsgesellschaft mbH; Weinheim; Germany.

Gorman, J. et al; "The Igx 3' Enhancer Influences the Ratio of Igx Versus Igλ B Lymphocytes"; Immunity: Sep. 1996; pp. 241–252; vol. 5; Cell Press.

Frippiat, J.–P. et al; "Organization of the Human Immunoglobulin Lambda Light–Chain Locus on Chromosome 22q11.2"; Human Molecular Genetics; 1995; pp. 983–991; vol. 4; No. 6; Oxford University Press.

Kawasaki, K. et al; "One–Megabase Sequence Analysis of the Human Immunoglobulin λ Gene Locus" Genome Research; 1997; pp. 250–261; vol. 7; Cold Spring Harbor Laboratory Press; New York, United States.

Giudicelli, V. et al; "IMGT, The International ImMunoGeneTics Database"; Nucleic Acids Research; 1997; pp. 206–211; vol. 25; No. 1; Oxford University Press.

Ignatovich, O. et al; "The Creation of Diversity in the Human Immunoglobulin $V_\lambda$ Repertoire"; Journal Molecular Biology; 1997; pp. 69–77; vol. 268; Academic Press Limited.

Combriato, G. et al; "$V_\lambda$ and $J_\lambda$–$C_\lambda$ gene segments of the human immunoglobulin λ light chain locus are separated by 14 kb and rearrange by a deletion mechanism"; Eur. J. Immunol.; 1991; pp. 1513–1522; vol. 21; Verlagsgesellschaft mbH; Weinhiem; Germany.

Foster, S. et al; "Molecular Mechanisms and Selective Influences that Shape the Kappa Gene Repertoire of IgM B Cells"; J. Clinical Investigation; Apr. 7, 1997; pp. 1614–1627: vol. 99; No. 7; The American Society of Clinical Investigation, Inc.

Bridges, S.I., et al; "Somatic Mutation and CDR3 Lengths of Immunoglobulin κ Light Chains Expressed in Patients with Rheumatoid Arthritis and in Normal Individuals"; The Journal of Clinical Investigation, Inc.; Aug. 1995; pp. 831–841; vol. 96; The American Society of Clinical Investigation, Inc.

Victor, K. et al; "Limited Junctional Diversity in κ Light Chains"; Journal of Immunology; 1994; pp. 3487–3475; vol. 152; The American Association of Immunologists.

Davies, N. et al; "Human Antibody Repertoires in Transgenic Mice: Manipulation and Transfer of YACs"; Antibody Engineering: A Practical Approach; 1996; pp. 1–35; Department of Development and Signalling; Brbraham Institute; Babraham, Cambridge; United Kingdom.

Hogan, B. et al; "Manipulating the Mouse Embryos: A Laboratory Manual"; 1994; Cold Spring Harbor Laboratory Press; United States of America.

Zou, X. et al; "Subtle Difference in Antibody Responses and Hypermutation of λ Light Chains in Mice with a Disrupted κ Constant Region"; Eur. J. Immunology; 1995; pp. 2154–2162; vol. 25; Verlsgsgesellschaft mbH; Weinheim: Germany.

Wurst, W. et al; "Production of Targeted Embronic Stem Cell Clones"; Gene Targeting: A Practical Approach; 1993; pp. 33–81; IRL Press; Oxford.

Hermann, B. et al; "A Large Inverted Duplication Allows Homologous Recombination Between Chromosomes Heterozygous for the Proximal t Complex Inversion"; Cell; 1987; pp. 813–825; vol. 48.

Galfrě, G. et al; "Preparation of Monoclonal Antibodies: Strategies and Procedures"; Methods in Enzymology; 1961; pp. 3–48; vol. 73; Academic Press, Inc.

Tijssen, P. et al; "Practice and Theory of Enzyme Immunoassays"; Laboratory Techniques in Biochemistry and Molecular Biology; 1985; vol. 15, Burdon, R.H. and Knippenberg, P.H. (eds); Elsevier; Amsterdam, The Netherlands.

Chomczynski, P. et al; "Single–Step Method of RNA Isolation by Acid Guanidinium Thiocyanate–Phenol–Chloroform Extraction"; Analytical Biochemistry; Apr. 1987; pp. 158–159; vol. 162; No. 1; The Academic Press, Inc. New York, United States.

Frohman, M. et al; "Rapid Production of Full–Length cDNAs from Rare Transcripts: Amplification Using a Single Gene–Specific Oligonucleotide Primer"; Proc. Natl. Acad. Sci.; Dec. 1988; pp. 8998–9002; vol. 85.

Ausubel, F.M. et al; "Current Protocols in Molecular Biology"; 1995; vol. 1Wiley & Sons, United States.

Williams, S. et al; "Sequence and Evolution of the Human Germline $V_\lambda$ Repertoire"; J. Mol. Biol.; 1996; pp. 220–232; vol. 264; Academic Press Limited.

Chen, J. et al; "B Cell Development in Mice that Lack One or Both Immunoglobulin κ Light Chain Genes"; The EMBO Journal; 1997; pp. 821–830; vol. 12, No. 3; Oxford University Press; United Kingdom.

Brüggemann, M. et al; "Strategies for Expressing Human Antibody Repertoires in Transgenic Mice"; Immunology Today; Aug. 1996; pp. 391–397; vol. 17; Elsevier Sciences Ltd.

Green, L. et al; "Regulation of B Cell Development by Variable Gene Complexity in Mice Reconstituted with Human Immunoglobulin Yeast Artificial Chromosomes"; J. Exp. Med.; Aug. 3, 1998; pp. 483–495; vol. 183; No. 3; The Rockefeller University Press.

Zou, X. et al; "Dominant Expression of a 1.3 Mb human Igx Locus Replacing Mouse Light Chain Production"; The FASEB Journal; Aug. 1996; pp: 1227–1232; vol. 10.

Xian, J. et al; "Comparison of the Performance of a Plasmid–Based Human Igx Minllocus and Yac–Based Human Igx Transloci for the Production of Human Antibody Repertoires in Transgenic Mice"; Transgenic; 1998; pp. 333–343: vol. 2; OPA; Malaysia.

Gonzalez–Fernandez; A. et al; "Somatic Mutation of Immunoglobulin λ Chains: A Segment of the Major Intron Hypermutates as Much as the Complementarity—Determining Regions"; Proc. Natl. Acad. Sci.; Dec. 1994; pp. 12614–12618; vol. 91.

Li, Y.S. et al; "The Regulated Expression of B Lineage Associated Genes During B Cell Differentiation in Bone Marrow and Fetal Liver"; J. Exp. Med; Sep. 1993; pp. 951–980; vol. 178; The Rockefeller University Press.

Hardy, R. et al; "Resolution and Characterization of Pro–B and Pre–Pro–B Cell Stages in Normal Mouse Bone Marrow"; J. Exp. Med.; May 1991; pp. 1213–1225; vol. 173; The Rockefeller University Press.

Saitta, M. et al; "Reference Values for Immunoglobulin Kappa and Lambda Light Chains and the Kappa/Lambda Ratio in Children's Serum"; Clinical Chemistry; 1992; pp. 2454–2457; vol. 38; No. 12.

Hood, L. et al; "Rabbit Antibody Light Chains and Gene Evolution"; Nature; Dec. 12, 1970; pp. 1040–1044; vol. 228.

Lansord, R; "Mechanism and Control of Immunoglobulin Gene Rearrangement"; B.D. Harnes and D.M. Glover (eds); pp. 1–100; IRL Press; New York; United States.

Nadel, B. et al; "Murine Lambda Gene Rearrangements: The Stochastic Model Prevails Over the Ordered Model"; The EMBO Journal; 1990; pp. 435–440; vol. 9; No. 2; Oxford University Press; United Kingdom.

Arakawa, H.; et al; "Re–evaluation of the Probabilities for Productive Rearrangements on the κ and λ Loci"; International Immunology; 1996; pp. 91–99; vol. 8; No. 1; Oxford University Press.

Giudicelli, V. et al; "IMGT, The Internation ImMunoGene Tics Database"; Nucleic Acids Research; 1997; pp. 206–211; vol. 26; No. 1; Oxford University Press.

Eagle, H.; "Propagation in a Fluid Medium of a Human Epidemoid Carcinoma, Strain KB"; Proceedings of the Society for Experimental Biology and Medicine; 1955; pp. 362–364; vol. 89; New York.

Taub, R. et al; "Variable Amplification of Immunoglobulin λ Light–Chain Genes in Human Populations"; Nature; Jul. 14, 1983; pp. 172–174; vol. 304; Macmillan Journals Ltd.

* cited by examiner

FIG. 5A

```
                    60              75              CDR1            90                  105
          GCC AGC ATC ACC TGC TCT GGA GAT AAA TTG GGG GAT AAA TAT GCT TGC TGG TAT CAG CAG AAG CCA
3-1       ... .A. ... ... ..T ... ... ... ... ... ..G ... ... ... ... ... ... ... ... ... ... :
14/9 Vλ07
                   210             225             240                 255
          TCT GGG AAC ACA GCC ACT CTG ACC ATC AGC GGG ACC CAG GCT GAC GAG GCT GAC TAT TAC TGT
          ... ... ... ... ... ... ... ... ... ... ... ... ... ... ... ... ... ... ... ..T ... :

60              75              CDR1            90                  105
          GCC AGC ATC ACC TGC TCT GGA GAT AAA TTG GGG GAT AAA TAT GCT TGC TGG TAT CAG CAG AAG CCA
3-1       ... ... ... ... ... ..G A.. ... ... ... ... .A .C. ... ... ..T .C. ... ... ... ... :
14/9 Vλ03
                   210             225             240                 255
          TCT GGG AAC ACA GCC ACT CTG ACC ATC AGC GGG ACC CAG GCT GAC GAG GCT GAC TAT TAC TGT
          ... ... ... ... ... G.. ... ... ... ..C ... ... ... ... ... ..T ... ... ... .G. ... :

60              75              CDR1            90                  105
          GCC AGG ATC ACC TGC TCT GGA GAT GCA TTG CCA AAA TAT GCT TAT TGG TAC CAG CAG AAG TCA
3-10      ... ... ... ... ... ... ... ... ... ... ... ... ... ... ... ... ... ... ... ... ... :
PP 05
                   210             225             240                 255
          TCA GGG ACA ATG GCC ACC TTG ACT ATC AGT GGG GCC CAG GTG GAG GAT GAA GCT GAC TAC TAC TGT
          ... ... ... ... ... ... ... ... ... ... ... ... ... ... ... ..A ... ... ... ... ... :
```

FIG. 5B

```
                                                    CDR2
                        135                  150                    165                       180                      195
120
GGC CAG TCC CCT GTG CTG GTC ATC TAT CAA GAT AGC AAG CGG CCC TCA GGG ATC CCT GAG ACC AAG CTG ACC GTC CTA        TTC TCT GGC TCC AAC ...>
... ... ... ... ... ... ... ... ... A.T ... ... ... ... ... ... .A. .G. ... ... ... ... ... ... ...
        CDR3
                     270                   285
CAG GCG TGG GAC AGC AGC ACT GCA          T TGG GTG TTC GGC GGA GGG ACC AAG CGG CCC TCA GGG ATC CCT GAG CGA TTC TCT GGC TCC AAC  Jλ3
... ... ... ... ... ... .C. ...          TGG GTA TTC GGC GGA GGG ACC TAC CTG ACC GTC CTG

CDR2
                        135                  150                    165                       180                      195
120
GGC CAG TCC CCT GTG CTG GTC ATC TAT CAA GAT AGC AAG CGG CCC TCA GGG ATC CCT GAG ACC AAG CTG ACC GTC CTA        TTC TCT GGC TCC AAC ...>
... ... ... ... ... ... ... ... ... ... ... ... ... ... ... ... ..A ... ... ... ... ... ... ... ...
        CDR3
                     270                   285
CAG GCG TGG GAC AGC AGC ACT GCA          T GTG GTA TTC GGC GGA GGG ACC AAG CGG CCC TCA GGG ATC CCT GAG CGA TTC TCT GGC TCC AAC  Jλ2
... ... ... ... ... .C. GC. ...          TG GTT TTC GGC GGA GGG ACC AAA CTG ACC ATC CTA

CDR2
                        135                  150                    165                       180                      195
120
GGC CAG GCC CCT GTG CTG GTC ATC TAT GAG GAC AGC AAA CGA CCC TCC GGG ATC CCT GAG AGA TTC TCT GGC TCC AGC ...>
... ... ... ... ... ... ... ... ... .C. ... ... ... ... ... ... ... ... ... ... ..A. ... ... ... ...
        CDR3
                     270                   285
TAC TCA ACA GAC AGC AGT GGT AAT CAT AG         T TGG GTG TTC GGC GGA GGG ACC AAG CTG ACC GTC CTA        JA3
... ... ... ... .A.. .C. ... ... ..            G GTG TTC GGC GGA GGG ACC AAG CTG ACC GTC CTA
```

FIG. 5C

```
                          60              75                         CDR1    90                    105
             ATC ACC ATC TCC TGC ACT GGA ACC AGC AGT GAC AGT GGT TAT AAC TAT GTC TCC TGG TAC CAA
2-14         ... ... ... ... ... ... ... ... ... ... ... ... ... ... ... .T. ... ... ... ...
PP 14
                    210              225             240                    255
             GGC TCC AAG TCT GGC AAC ACG GCC TCC CTG ACC ATC TCT GGG CTC CAG GCT GAG GAC GCT GAT
2-14         ... ... ... ... ... ... ... ... ... ... ... ... ... ... .C. ... ... ... ... ...
PP 14

60              75                         CDR1    90                    105
             GTC AGG ATC ACA TGC CAA GGA GAC AGC CTC AGA AGC TGG TAC TAT TAT GCA AGC TGG TAC CAG CAG AAG CCA
3-19         ... ... ... ... ... ... ... ... ... ... ... ... ... ... ... .T. ... ... ... ... ... ... ...
PP 02
                    210              225             240                    255
             TCA GGA AAC ACA GCT TCC TTG ACC ATC ACT GGG GCT CAG GCG GAA GAT GAG GCT GAC TAT TAC TGT
3-19         ... ... ... ... ... ... ... ... ... ... ... ... ... .A. ... ... ... ... ... ... ...
PP 02

60              75                         CDR1    90                    105
             ATC ACC ATC TCC TGC ACT GGA ACC AGC AGT GAT GTT GGC AGT TAT AAC CTT GTC TCC TGG TAC CAA
2-23         ... ... ... ... ... ... ... ... ... ... .G. ... ... ... ... ... .T.. ... ... ... ...
SORT 04
                    210              225             240                    255
             GGC TCC AAG TCT GGC AAC ACG GCC TCC CTG ACA ATC TCT GGG CTC CAG GCT GAG GAC GCT GAT
2-23         .C. ... ... ... ... ... ... ... ... ... ... ... ... ... ... ... ... ... ... ...
SORT 04
```

FIG. 5D

A human IgM,λ monoclonal anti-human PLAP 7783.26 from a 5-feature translocus mouse

MURINE EXPRESSION OF A HUMAN IGA LAMBDA LOCUS

This application claims priority to PCT/GB99/03632, filed Nov. 3, 1999, the entirety of which is hereby incorporated by reference.

BACKGROUND OF THE INVENTION

The light chain component of the Ig protein is encoded by 2 separate loci, Igκ and Igλ. The proportion of antibodies containing κ or λ light chains varies considerably between different species (1–3), e.g., in mice the κ:λ ratio is 95:5, compared to 60:40 in humans. Two models have evolved to account for this apparent bias in the expression of κ in the mouse. First, from the observation that murine Igλ-producing myelomas have rearranged κ light chain genes, and that Igκ producing cells have the λ light chain locus in germline configuration, it was proposed that κ rearrangement must occur before λ rearrangement can commence (4, 5). In the human situation, however, while almost all λ producing cells have both κ alleles rearranged, the proportion of κ and λ producing cells are similar (4). The second proposal is that κ and λ loci are both available for rearrangement at the same time, but the mouse κ locus is more efficient at engaging the rearrangement process (6). The occasional finding of cells with rearranged λ and the κ locus in germline configuration may support this (5, 7, 8). The influence of antigen selection on the biased κ:λ ratio is discounted by the finding that the ratio is similar in fetal liver and in cells that have not encountered antigen (9–13).

Light chain V-J rearrangement occurs at the transition from pre B-II to immature B cells, where the surrogate light chain associated with membrane Igμ is replaced by κ or λ light chain (14). Although the timing of light chain rearrangement is essentially defined, the processes which activate light chain locus rearrangement are not fully understood. From locus silencing experiments, it became clear that κ rearrangement is not a prerequisite for λ recombination (15). Indeed, κ and λ rearrangements are independent events (16), the activation of which may be affected by differences in the strength of the respective enhancers. A region believed to be important in the regulation of the accessibility of the human λ locus has been identified about 10 Kb downstream of Cλ7 (17, 18). Functional comparisons in reporter gene assays identified a core enhancer region that is flanked by elements which can drastically reduce enhancer activity in pre-B cells (17). Although transfection studies showed that the κ and λ 3' enhancer regions appear to be functionally equivalent, other (functional) sequences flanking the core enhancer motifs are remarkably dissimilar. Targeted deletion of the κ 3' enhancer in transgenic mice showed that this region is not essential for κ locus rearrangement and expression but is required to establish the κ:λ ratio (19).

The human Igλ locus on chromosome 22q11.2 is 1.1 Mb in size and typically contains 70 Vλ genes and 7 Jλ-Cλ gene segments (20, 21 and references therein). About half of the Vλ genes are regarded as functional and Jλ-Cλ1, 2, 3 and 7 are active. The Vλ genes are organized in 3 clusters which contain distinct V gene family groups. There are 10 Vλ gene families, with the largest VλIII being represented by 23 members. In human peripheral blood lymphocytes, the most J-C proximal V gene segments in cluster A, from families I, II and III, are preferentially rearranged, with the contribution of the 2a2 Vλ segment (2–14 in the new nomenclature (22) being unusually high (23). All λ gene segments have the same polarity which allows deletional rearrangement (24). Sequence diversity of the Igλ repertoire is provided mainly by Vλ-Jλ combination. Additional CDR3 diversity due to N (nonencoded)- or P (palindromic)-nucleotide additions at the V to J junction, although not as extensive as seen in IgH rearrangement, seems to be much more frequently used in humans than in mice (25, 26, 27, 28), where the TdT (terminal deoxyribonucleotide transferase) activity is down-regulated at the time of light chain rearrangement.

It has been shown that human Ig can be produced in transgenic mice carrying human Ig genes on miniloci or yeast artificial chromosomes (YACs) (58, 59, 60, 61, 62) and that silencing of the endogenous mouse heavy and κ loci enhances human antibody production in such transgenic animals. However, in all such mice reported to date, only the human κ light chain genes have been incorporated and there have been no reports of the human λ light chain locus being integrated into transgenic mice. Therefore, until the present invention, no λ-containing human antibodies have been made from transgenic mice, nor has there been any information on the expressibility of human λ genes in such animals or on the relative contributions of human κ and λ in mice carrying both transgenic human loci. Thus it was not known whether λ-transgenic mice would be suitable for the production of human antibodies.

SUMMARY OF THE INVENTION

It is an object of the present invention to provide transgenic animals, such as a mouse, that can express human λ sequences. In accomplishing this and other objects, there is provided, in accordance with one aspect of the invention, transgenic mice comprising as a translocus a YAC of about 410 Kb, wherein the YAC contains most of the human Vλ genes of cluster A and all the human Jλ-Cλ segments in germline configuration, wherein the translocus shows high expression, and is able to compete equally with the endogenous mouse κ locus.

There also is provided, in accordance with another aspect of the invention, transgenic mice comprising as a translocus a YAC of about 410 Kb, wherein the YAC contains most of the human Vλ genes of cluster A and all the human Jλ-Cλ segments in germline configuration, wherein the mouse has one or both endogenous Igκ alleles disrupted, and wherein the translocus shows high expression.

In accordance with yet another aspect of the invention, there are provided a transgenic mouse carrying a 380 Kb region of the human immunoglobulin (Ig) λ light (L) chain locus in germline configuration, wherein the introduced translocus resides on a yeast artificial chromosome (YAC) that accommodates the most proximal V (variable gene) λ cluster—with 15 V λ genes that contribute to over 60% of λ light chains in man—and all J λ-C λ segments with the 3' region including the downstream enhancer.

In accordance with still another aspect of the invention, there are provided transgenic mice comprising human Ig lambda genes in which the proportion of the κ and λ light chains expressed by said human lambda genes resembles that found in humans, and exhibits relative proportions of ≦60% κ light chains and ≧40% λ light chains.

The transgenic mice according to the invention can include a HuIgλ YAC that accommodates a 380 Kb region of the human λ light chain locus in authentic configuration with all Vλ genes of cluster A, the Jλ-Cλ segments and the 3' enhancer, such as the HuIgλ YAC shown in FIG. 1.

In accordance with a further aspect of the invention, there are provided methods for producing transgenic mice, comprising:

(a) introducing a HuIgλ YAC into murine embryonic stems cells; and
(b) deriving a transgenic mouse from the cells of step (a).

The HuIgλ YAC can be about 410 Kb and accommodate a 380 Kb region (Vλ-JCλ) of the human λ light chain locus with V, J and C genes in germline configuration when it is introduced into said stem cells. Additionally, selectable markers, such as two copies of the neomycin resistance gene (NEO$^r$) can be site-specifically integrated into the ampicillin gene on the left (centromeric) YAC arm in order to permit selection. The methods can further comprise steps where YAC-containing yeast cells are fused with HM-1 embryonic stem (ES) cells and G418 resistance colonies are picked and analyzed 2–3 weeks after protoplast fusion. The ES cells can contain a complete HuIgλ YAC copy, and can be used for blastocyte injection to produce a transgenic animal. The breeding of a transgenic animal with a Balb/c mouse, for example, results in germline transmission. Breeding partners include κ$^{-/-}$ mice to establish lines of transgenic mice.

In accordance with another aspect of the invention, there are provided hybridomas obtainable from HuIgλ YAC/κ$^{+/-}$ mice (preferably one that is 3 months old), for example, by fusion of splenocytes with NSO myeloma cells, and subsequent selection of single clones. Antibodies obtainable from these hybridomas also are provided.

In accordance with another aspect of the invention, there is provided transgenic mice comprising as a translocus a yeast artificial chromosome (YAC) of greater than 100 Kb which contains a proportion of the human Vλ genes proximal to the Jλ-Cλ cluster in germline configuration. The YAC can include a 380 Kb region of the human Igλ locus in authentic configuration with most Vλ genes of cluster A, Jλ-Cλ segments and the 3' enhancer.

In accordance with yet another aspect of the invention, there are provided transgenic mice comprising variable, joining and constant genes of the human λ light chain locus as a transgenic locus on a YAC, wherein B cells of said mice rearrange said λ light chain genes and the mice express serum immunoglobulins containing human λ light chains. the λ translocus is rearranged with similar efficiency as endogenous mouse κ and at the same time as or before the endogenous κ locus. Additionally, the endogenous κ locus can be silenced, and the mouse expresses serum immunoglobulins containing human λ light chains. The transgenic mice can further comprise human heavy chain genes as a second transgenic locus integrated on a separate YAC, wherein the mice express serum immunoglobulin molecules containing combinations of human heavy and λ light chains. Moreover, the second transgenic locus can carry a diversity of human heavy chain constant region genes, including μ, δ and γ genes. For example, the heavy chain transgenic locus can carry a diversity of human heavy chain constant region genes, including μ, δ and γ genes, in authentic germline configuration. Also permissible are transgenic mice carrying human λ light chain genes, wherein the mice comprise human κ light chain genes as a second transgenic light chain locus integrated on a separate YAC, wherein the mice express serum immunoglobulin molecules containing human κ and λ light chains. Additionally, there are provided transgenic mice carrying human λ light chain genes comprising human heavy chain genes as a second transgenic locus and human κ light chain genes as a third transgenic locus, wherein the mice express serum immunoglobulin molecules containing human heavy chains in combination with human κ or λ light chains. Expression of the endogenous mouse heavy and/or light chain loci in the transgenic mice of the invention can be prevented, if desired, through gene targeting or other means and which expresses serum immunoglobulin containing human heavy and/or light chains and which are deficient in production of mouse immunoglobulin.

In accordance with still a further aspect of the invention, there are provided transgenic mice carrying human λ light chain genes in which expression of the human λ locus is equal to or greater than that of the endogenous or transgenic human κ locus. The λ translocus can be bred to homozygosity. Additionally, the there can be rearranged variable genes in the λ translocus are subject to somatic hypermutation.

In accordance with yet a further aspect of the invention, there are provided methods for production of human antibodies comprising stimulating with antigen transgenic mice incorporating human λ light chain genes into their genome and collecting the human antibodies which bind to the antigen. Hybridomas for the production of antibodies can be created through fusion to an appropriate mouse myeloma cell line.

In accordance with still a further aspect of the invention, there are provided human monoclonal antibodies comprising human heavy and light chains of diverse isotypes and chain combinations produced from transgenic mice carrying the human λ translocus. The variable regions of the human λ light chains of such antibodies can undergo somatic mutation. The antibodies preferably have an affinity for antigen of greater than $10^8$ M.

These and other aspects of the invention will become apparent to the skilled person upon a review of the specification, including the examples, figures and sequences.

BRIEF DESCRIPTION OF THE FIGURES

FIG. 5 shows human Vλ sequences from sorted B220$^+$ and PNA$^+$ Peyer's patches B-cells from HuIgλ$^+$YAC/κ$^{+/-}$ mice (SEQ ID NOS 5, 6, 7, 8, 5, 9, 10, 11, 12, 13, 7, 14, 15, 16, 7, 17, 18, 19, 10, 20, 21, 22, 7, and 23 respectively in order of appearance).

DETAILED DESCRIPTION OF ASPECTS OF THE INVENTION

Figure 1:
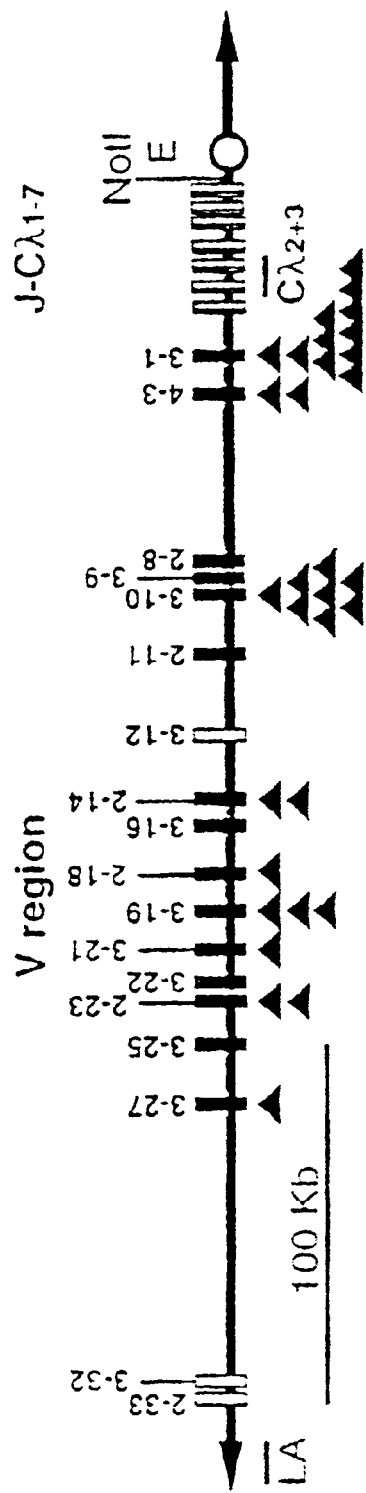
FIG. 1 shows that the HuIgλYAC accommodates a 380 Kb region of the human λ light chain locus in authentic configuration with all Vλ genes of cluster A (21, 40, 54), the Jλ-Cλ segments and the 3' enhancer (17). Black boxes represent functional Vλ genes (3–27, 3–25, 2–23, 3–22, 3–21, 3–19, 2–18, 3–16, 2–14, 2–11, 3–10, 3–9, 2–8, 4–3, 3–1) and white boxes show Vλ genes with open reading frames (2–33, 3–32, 3–12) which have not been identified in productive rearrangements of human lymphocytes (40). Pseudogenes are not shown. Black triangles indicate rearranged V genes found by RT-PCR in spleen and sorted Peyer's patch cells from HuIgλ mice. The unique NotI restriction site is indicated. Probes to assess the integrity of the HuIgλYAC, LA (left arm) and Cλ2+3 are indicated.

The present invention provides transgenic mice ('lambda mice', or 'λ mice') into which a YAC of about 410 Kb has been introduced as a transgenic locus (translocus) containing most of the human Vλ genes of cluster A and all the Jλ-Cλ segments in germline configuration. As the skilled person will recognize, sizes of polynucleotides provided herein are approximate, and can be readily changed in view of the teachings contained herein without departing from the invention.

The translocus leads to high expression of human λ light chains in plasma and on B cells and is able to compete equally with the endogenous mouse κ locus. A number of different transgenic mice are further described in which the human λ light chain is present in different combinations with YACs encoding genes of the human heavy chain locus (IgH) and genes of the human κ light chain locus (Igκ), and in which the endogenous mouse alleles for heavy chain or κ light chain may have been disrupted. Mice with these features are suitable for the production of fully human antibodies carrying the λ light chain. After immunization with antigens, such mice produce fully human antibodies containing the λ light chain with at least as high a frequency as they do κ-containing antibodies, and often with an excess of λ-containing antibodies over κ. Moreover, the mice according to the invention can be used to produce antigen specific monoclonal human λ-containing antibodies of high affinity. Isolation of human Vλ genes from the transgenic mice by RT-PCR cloning showed that many Vλ genes are rearranged and exhibit somatic hypermutation. Such DNA products can be used to construct human λ-containing antibodies for expression in prokaryotic or eukaryotic cells. Thus human λ-expressing transgenic mice provide an improved method of producing fully human antibodies, either from hybridomas or by in vitro recovery and manipulation of V λ genes.

The present invention provides the first transgenic mice carrying unrearranged human Ig λ genes on a YAC as a translocus. They demonstrate that the human λ genes are well-expressed in the translocus mouse similar to or better than their expression in man relative to κ. The λ-containing antibodies made by such translocus mice may be of value as therapeutic reagents.

According to the invention, transgenic mice were created carrying a 380 Kb region of the human immunoglobulin (Ig) λ light (L) chain locus in germline configuration. The introduced translocus on a yeast artificial chromosome (YAC) accommodates the most proximal V (variable gene) λ cluster—with 15 Vλ genes that contribute to over 60% of λ light chains in man—and all Jλ-Cλ segments with the 3' region including the downstream enhancer. The HuIgλYAC mice were bred with animals in which mouse κ L chain production was silenced by gene targeting. Human Igλ expression in mouse κ$^{-/-}$ animals was dominant with up to 84% of B220$^+$ B-cells expressing surface human L chain. In serum human Igλ was up to 1.9 mg/ml, while mouse L chain levels were reduced to 0.2 mg/ml. However, a striking result was that in heterozygous κ$^{+/-}$ and normal κ$^{+/+}$ translocus mice both human λ and mouse κ were expressed at similar high levels (38% and 45% of cells, respectively). Interestingly, in HuIgλYAC/Moκ mice human λ is predominantly expressed at the pre B-cell stage with subsequent upregulation of cells expressing mouse L chain at the immature B-cell stage. The human Vλ genes hypermutate readily but show restricted P or N sequence variability at the V-J junction. The finding that human λ genes can be utilized with similar efficiency in mouse and man implies that L chain expression is dependent on the configuration of the locus. Thus, the transfer of large transloci may circumvent many expression problems encountered with small gene constructs introduced into cells and animals, with the advantage that some silencing approaches such as exploiting human antibody production may prove unnecessary.

Furthermore, the λ-expressing transgenic mice with the κ$^{-/-}$ background were mated with those in which the human heavy (H) chain genes were incorporated as a translocus (65) and in which the endogenous mouse H chain locus had been silenced by the µMT$^{-/-}$ modification (57), producing so-called '4-feature'λ-mice (human H and λ transloci on a endogenous H and κ knockout background). These mice produced human IgM, λ immunoglobulin in their plasma and responded to immunization by production of human IgM,λ antibodies. The mice were further crossed with those having, in addition to the other characteristics, the human κ genes as a YAC translocus (65) to produce mice which express both human IgM,λ and IgM,κ antibodies, so called '5-feature' mice. In these animals, the B lymphocyte population shows preferential (3:1) expression of human λ over human κ. Human IgM is found in the serum at between 50 and 400 μg per ml. The 5-feature mice were immunized with several different antigens, including human antigens, leading to production of specific human antibodies in their serum. Hybridomas secreting fully human monoclonal antibodies were prepared from the spleen cells of such mice. Among such hybridomas, the ratio of λ:κ is often in favor of λ, in some cases by as much as 8:1. This is remarkable in view of the κ bias (60κ:40 λ) seen in normal human plasma and the extreme κ bias (95κ:5λ) in plasma of normal mice. Thus, transgenic mice have been produced in which the proportion of λ to κ light chains resembles or exceeds that normally found in humans. In general, transgenic loci are not highly expressed in authentic fashion or as well as endogenous genes. Moreover, in normal mice the endogenous λ genes are not efficiently expressed and it was therefore assumed that other λ genes would also be expressed at low frequency. Thus, the equally high expression in man and mouse of human λ is very unexpected and could not have been predicted.

The 4 and 5 feature λ mice develop a highly effective repertoire of λ-containing antibodies which can be used to make hybridomas and monoclonal antibodies of high affinity. The λ translocus undergoes somatic hypermutation and could therefore contribute to increased antibody affinity. Also described herein is a human monoclonal antibody, anti-human placental alkaline phosphatase (PLAP), with a λ light chain from a 5-feature mouse, with an affinity of greater than $10^8$ $M^{-1}$. Thus, according to the invention there have produced mice suitable for immunization with human antigens and for the isolation of high affinity human antibodies containing λ light chains which are suitable for therapeutic applications.

The present invention is further illustrated by the following examples, which do not limit the invention in any manner or way.

EXAMPLE I

Production Methodologies
The HuIgλYAC, Introduction Into ES Cells and Derivation of Transgenic Mice.

The 410 Kb HuIgλYAC, accommodating a 380 Kb region (Vλ-JCλ) of the human λ light chain locus with V, J and C genes in germline configuration, was constructed as described (29). To allow selection, 2 copies of the neomycin resistance gene (NEO$^r$) were site-specifically integrated into the ampicillin gene on the left (centromeric) YAC arm. YAC-containing yeast cells were fused with HM-1 ES cells, a kind gift from D. Melton, as described (30) and G418 resistant colonies were picked and analyzed 2–3 weeks after protoplast fusion. ES cells containing a complete HuIgλYAC copy, confirmed by Southern hybridization, were used for blastocyst injection to produce chimeric animals (31). Breeding of chimeric animals with Balb/c mice resulted in germiline transmission. Further breeding with κ$^{-/-}$ mice (32) established the lines for analysis.
Southern Blot Analysis.

Either conventional DNA was obtained (33) or high molecular weight DNA was prepared in agarose blocks (34). For the preparation of testis DNA, tissues were homogenized and passed through 70 μM nylon mesh. PFGE conditions to separate in the 50–900 Kb range were 1% agarose, 180V, 70 s switch time and 30 hours running time at 3.5° C. Hybridization probes were Cλ2+3 and the left YAC arm probe (LA) comprising LYS2 (29).
Production of 4 and 5 Feature Mice The 4 and 5 feature mice were produced by crossing the transgenic λ mice with transgenic mice described previously carrying the IgH YAC and the Igκ YAC as transloci, and in which the endogenous loci for H and κ were disrupted (μMT$^{-/-}$, Moκ$^{-/-}$ knockouts) (65 and references therein). The transgenic status of the offspring was confirmed by Southern hybridization of genomic DNA with appropriate probes. The strains were bred to homozygosity to carry 2 alleles of each of the transloci and for each of the knockout features. Test breeding showed that the 3 transloci and 2 knockouts were not linked.
Immunization of Mice, Hybridoma Production and ELISA Assay Four and 5 feature mice were initially immunized with 50 μg of antigen in complete Freund's adjuvant and boosted at 4 and 8 weeks with 50 μg in IFA. A final boost was given at 12 weeks and 3 days later hybridomas were prepared by fusion of splenocytes with NS/0 myeloma cells using polyethylene glycol. Fusion supernatants were screened for reactivity with the immunogen by ELISA and selected clones expanded for further analysis and cloned. Human IgM expression levels and light chain isotype were determined by ELISA. Specificity of hybridomas was confirmed by testing for cross-reactivity to unrelated antigens.

Affinity determination was performed by the method of Friguet et al. (63), i.e. a fixed concentration of antibody was incubated with varying amounts of PLAP to equilibrium in tubes and the free antibody determined by quantitative ELISA on an PLAP-coated microwell plate. The free and bound antibody concentrations were calculated and the Scatchard plot of B/F antigen versus B antigen was plotted. The affinity was given by the slope of the graph.

For the detection of human or mouse Igλ, coating reagents were a 1:500 dilution of anti-human λ light chain monoclonal antibody (mAB) HP-6054 (L 6522, Sigma, St. Louis, Mo.) or a 1:500 dilution of the 2.3 mg/ml rat anti-mouse λ mAB (L 2280, Sigma), respectively. Respective binding was detected with biotinylated antibodies: polyclonal anti-human λ (B 0900, Sigma), a 1:1000 dilution of polyclonal anti-mouse λ (RPN 1178, Amersham Intl., Amersham, UK) or rat anti-mouse Igλ (# 021172D, Pharmingen, San Diego, USA) followed by streptavadin-conjugated horseradish peroxidase (Amersham). Mouse IgG2aλ myeloma protein from HOPC1 (M 6034, Sigma) and human serum IgGλ (I 4014, Sigma) were used to standardize the assays. To determine mouse κ light chain levels, plates were coated with a 1:1000 dilution of rat anti-mouse κ, clone EM34.1 (K 2132, Sigma), and bound Ig was detected using biotinylated rat mAB anti-mouse Igκ (Cat. no. 04-6640, Zymed, San Francisco). Mouse myeloma proteins IgG2aκ and IgG1κ (UPC10 and MOPC21, Sigma) were used as standards. For detection of mouse IgM, plates were coated with polyclonal anti-mouse μ (The Binding Site, Birmingham, UK) and bound Ig was detected with biotinylated goat anti-mouse μ (RPN1176, Amersham) followed by streptavadin-conjugated horseradish peroxidase. Mouse plasmacytoma TEPC183, IgMκ, (Sigma) was used as a standard.
Flow Cytometry Analysis.

Cell suspensions were obtained from bone marrow (BM), spleen and Peyer's patches (PPs). Multicolor staining was then carried out with the following reagents in combinations illustrated in FIG. 4: FITC-conjugated anti-human λ (F5266, Sigma), PE-conjugated anti-mouse c-kit (CD117) receptor (clone ACK45, cat. no. 09995B, Pharmingen, San Diego, USA), PE-conjugated anti-mouse CD25 (IL-2 receptor) (Sigma, clone 3C7, P 3317), biotin-conjugated anti-human κ (clone G20-193, cat. no. 08172D, Pharmingen), biotin-conjugated anti-mouse CD19 (clone 1D3, cat. no. 09654D, Pharmingen), followed by Streptavadin-Quantum Red (S2899, Sigma) or Streptavadin-PerCP (cat. no. 340130, Becton-Dickinson) and rat monoclonal anti-mouse κ light chain (clone MRC-OX-20, cat. MCA152, Serotec, Oxford, UK) coupled according to the manufacturer's recommendations with allophycocyanin (APC) (PJ25C, ProZyme, San Leandro, USA). Data were collected from $1 \times 10^6$ stained cells on a FACScalibur flow cytometer (Becton Dickinson Immunocytometry Systems, Mountain View, Calif., USA) as described (32). Cells were first gated on forward and side scatter to exclude dead cells. To obtain accurate percentage distribution for comparison, cells from normal mice were stained in parallel. In addition, human peripheral blood lymphocytes were purified on Ficoll gradients (1.077 g/ml) and stained with PE-conjugated anti-human CD19 antibody (P7437, clone SJ25-C1, Sigma), biotinylated anti-human κ followed by Streptavadin-Quantum Red and FITC-conjugated anti-human λ antibodies as above.

For RT-PCR cloning of Vλ genes PPs cells were stained with FITC-conjugated peanut agglutinin (PNA) (L 7381, Sigma) and PE-conjugated anti-mouse B220 antibodies (Sigma P 3567). Double-positive cells were sorted on the FACStar$^{Plus}$ flow cytometer (Becton Dickinson Immunocytometry Systems, Mountain View, Calif.) as described (32) and $5 \times 10^3$ cells were lysed in denaturing solution (37). 5'RACE was carried out as described below with 1 modification—2 μg carrier RNA was added to the cell lysates before RNA extraction and precipitation.

Cloning and Sequencing of 5'RACE Products.

Spleen RNA was prepared as described (37) and for cDNA preparation 2–3 μg of RNA was ethanol precipitated and air-dried. For rapid amplification of 5' cDNA ends (5'RACE) (38) first strand cDNA was primed with oligo (dT)22 and 100 units of Super Script II reverse transcriptase (Gibco BRL, Gaithersburg, Md.) was used at 46° C. according to manufacturer's instructions with 20 units of RNAse placental inhibitor (Promega, Madison, Wis.). The DNA/RNA duplex was passed through 1 ml G-50 equilibrated with TE (10 mM Tris-HCl pH 7.8, 1 mM EDTA) in a hypodermic syringe to remove excess oligo(dT). For G-tailing 20 units of TdT (Cambio, Cambridge, UK) were used according to standard protocols (39). Double stranded (ds) cDNA was obtained from G-tailed ss cDNA by addition of oligonucleotide Pr1 (see below), 100 μM dNTP and 2.5 units of Klenow fragment (Cambio) and incubation for 10 min at 40° C. After heating the reaction for 1 min at 94° C. and extraction with phenol-chloroform the ds cDNA was passed through G-50 to remove primer Pr1. PCR amplifications, 35 cycles, were carried out in the RoboCycler Gradient 98 Thermal Cycler (Stratagene, LaJolla, Calif., USA) using oligonucleotides Pr2 and Pr3. For PCR of PPs cDNA 50 cycles were used: 40 cycles in the first amplification and 10 cycles in additional amplifications. Pfu Thermostable Polymerase (Stratagene, LaJolla, Calif., USA) was used instead of Taq polymerase to reduce PCR error rates. The amplification products were purified using a GENECLEAN II kit (BIO 101, Vista, Calif., USA) and re-amplified for 5 cycles with primers Pr2 and Pr4 to allow cloning into Eco RI sites. Oligonucleotide for 5'RACE of V□ genes were:

Pr1 5'-AATTCTAAAACTACAAACTG CCCCCCCCA/T/G-3' (SEQ ID NO: 1)

Pr2 5'-AATTCTAAAACTACAAACTGC-3' (SEQ ID NO: 2) (sense)

Pr3 -5'-CTCCCGGGTAGAAGTCAC-3' (SEQ ID NO: 3) (reverse)

Pr4 5'-AATTCGTGTGGCCTTGTTGGCT-3' (SEQ ID NO: 4) (reverse nested).

A PCR protocol (A. Sudarikov) was used to clone Vλ PCR products. PCR products of about 500 bp were cut out from agarose gels and purified on GENECLEAN II. The DNA was incubated in 50 mM Tris-HCl, pH 7.4, 10 mM MgCl$_2$, with 100 μM dGTP/dCTP and 1 unit of Klenow fragment for 10 min at RT. Under these conditions the Klenow fragment removes the 3' ends of the PCR products (AATT) leaving ligatable Eco RI overhangs. DNA was ligated with Eco RI restricted pUC19, transformed into competent E. coli XL1Blue and colonies were selected on X-Gal/IPTG/amp plates. Plasmid DNA prepared from white colonies was used for sequencing. Sequencing of both strands was done on the ABI 373 automated sequencer in the Babraham Institute Microchemical Facility.

EXAMPLE 2

Characterization of the Transgenic Mice, Production Methodologies and Produced Antibodies The transgenic human Igλ locus. The human Igλ translocus (FIG. 1) was assembled on a YAC by recombining 1 YAC containing about half of all Vλ gene segments with 3 overlapping cosmids containing Vλ and Jλ-Cλ gene segments and the 3' enhancer (29). This resulted in a 410 Kb YAC accommodating a 380 Kb region of the human λ light chain locus with 15 Vλ genes regarded as functional, 3 Vλs with open reading frames but not found to be expressed and 13 Vλ pseudogenes (40). This HuIgλYAC was introduced into ES cells by protoplast fusion (30) and chimeric mice were produced by blastocyst injection (31). The ES cell clone used for this showed a 450 Kb NotI fragment corresponding to HuIgλYAC, as identified by PFGE and Southern hybridization with the 3' probe, Cλ2+3, and the 5' probe, LA comprising LYS2, present in the left centromeric YAC arm (not shown). Germline transmission was obtained, and PFGE analysis of testis DNA from 1 animal is illustrated in FIG. 2. A NotI fragment larger than 380 Kb is necessary to accommodate this region of the HuIgλYAC and the 450 Kb band obtained indicates random integration involving the single NotI site 3' of Jλ-Cλ and a NotI site in the mouse chromosome. Digests with EcoRI/HindIII and hybridization with the Cλ2+3 probe further confirmed the integrity of the transferred HuIgλYAC (FIG. 2). The results indicated that one complete copy of the HuIgλYAC was integrated in the mouse genome.

Human Igλ Expression is Dominant in Mouse κ$^{-/-}$ Animals.

Figure 3:
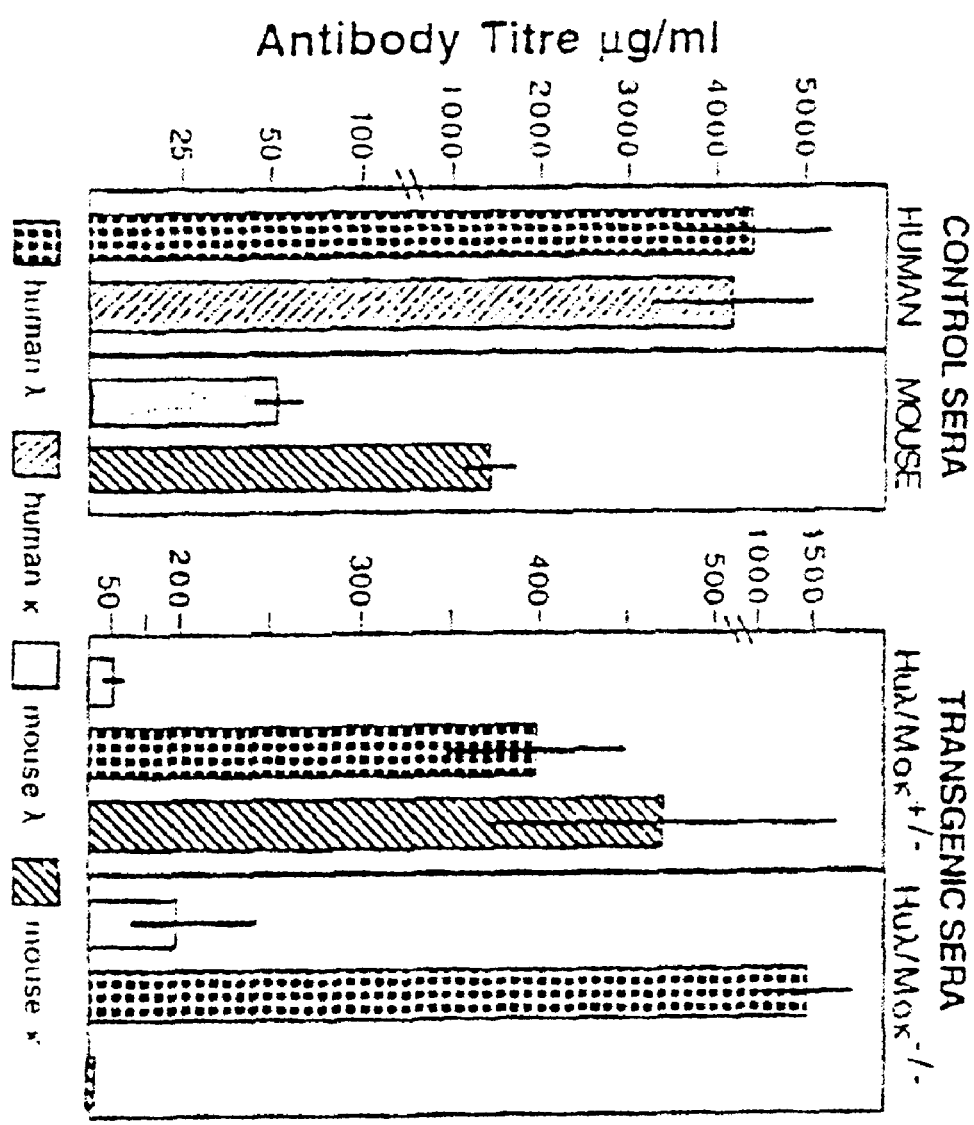
FIG. 3 shows human Igλ, mouse Igκ and mouse Igλ serum titers for HuλYAC/Moκ$^{+/-}$ and HuλYAC/Moκ$^{-/-}$ mice (5–6 mice per group kept in pathogermfree conditions and 5 human sera). Antibody levels presented were obtained from 2–3 months old animals but the serum titers from older mice were similar. From the 5 HuλYAC/Moκ$^{+/-}$ mice tested 3 animals had somewhat higher mouse Igκ titers than human Igλ while 2 animals showed higher human Igλ levels. The controls show light chain distribution in human and normal mouse serum. Total Ig levels are in good agreement with the sum of individual titers (not shown).

To assess the human λ light chain repertoire for the production of authentic human antibodies the HuIgλYAC mice were bred with mice in which endogenous Igκ production was silenced by gene targeting (32). In these κ$^{-/-}$ mice, the mouse Igλ titers are elevated compared to κ$^{+/+}$ strains (32, 41). Serum titrations (FIG. 3) showed that human Igλ antibody titers in HuIgλYAC/κ$^{-/-}$ mice are between 1 and 2 mg/ml which in some cases is up to 10-fold higher than the mouse Igλ levels. Interestingly, the mouse Igλ levels remained low in the HuIgλYAC/κ$^{-/-}$ mice, similar to the levels found in normal mice. High levels of human Igλ$^+$ cells were also identified in flow cytometric analysis of splenic B-cells from HuIgλYAC/κ$^{-/-}$ mice (FIG. 4A) with human λ expressed on the surface of >80% of the B-cells while the number of mouse Igλ$^+$ cells was always below 5% (data not shown).

Human Igλ Expression Equals Mouse Igκ Production.

Assessment of human Igλ production in heterozygous HuIgλYAC$^{+}$/κ$^{+/-}$ mice allowed a detailed comparison of expression and activation of endogenous versus transgenic light chain loci present at equal functional numbers. Serum analysis (FIG. 3) of mice capable of expressing both human λ and mouse κ showed similar titers for human and mouse light chains. Human Igλ levels in HuIgλYAC/κ$^{+/+}$ transgenic mice were very similar to those in HuIgλYAC/κ$^{+/-}$ mice. Total Ig levels in HuIgλYAC$^{+}$/κ$^{+/-}$ mice were 1–2 mg/ml, with a typical contribution of about 51% mouse Igκ, 43% human Igλ and 6% mouse Igλ. However, a comparison of endogenous κ and human λ expression in individual sera from HuIgλYAC mice, and similarly from human volunteers, showed that λ/κ ratios can vary. For example, 3 of the HuIgλYAC/κ$^{+/-}$ mice produced somewhat higher κ levels while in 2 mice the human λ levels were higher than the Igκ titers. In HuIgλYAC/κ$^{+/-}$ mice, similar high translocus expression was also found in B220$^{+}$ B-cells from different tissues, for example 38% of spleen cells expressed human λ and 45% mouse κ (FIG. 4A). These values resemble very much the levels in human volunteers as illustrated in FIG. 4A with 34% Ig λ$^{+}$ versus 51% Igκ$^{+}$ in CD19$^{+}$ peripheral blood lymphocytes.

To assess whether the high contribution of the human λ translocus to the mature B cell repertoire is the result of selection at the mature B-cell stage, or alternatively from early translocus rearrangement, light chain expression in bone marrow precursor B-cells was examined. For this, early B-cell markers, c-kit or CD25, were used in 4-color stainings in combination with the B-cell lineage marker CD19 and human λ and mouse κ specific antibodies. FIG. 4B shows that human λ expression in HuIgλYAC/κ$^{+/-}$ mice occurs at an earlier stage of development than mouse κ light chain expression. Human λ expression can be detected at the unusually early CD19$^{+}$/c-kit$^{+}$ pre B-I stage and is maintained in CD19$^{+}$/CD25$^{+}$ pre B-II cells. However, at the later immature to mature B-cell stage (CD19$^{+}$/c-kit$^{-}$/CD25$^{-}$) the proportion of mouse Igκ$^{+}$ cells is significantly increased. This suggests that human λ light chains can rearrange at an earlier stage than mouse Igκ but that upregulation at the mature B-cell stage balances any disadvantages in the timing of rearrangement.

DNA Rearrangement and Diversification of a Highly Active Human λ Translocus.

In order to assess whether the translocus expression levels were a direct result of its rearrangement capacity, individual hybridoma clones were analyzed. Results from 2 fusions suggest that human λ and mouse κ light chain producing cells were present in the spleen of HuIgλYAC/κ$^{-/+}$ mice at similar frequencies. Furthermore, the antibody expression rates of human λ (2–20 μg/ml) or mouse κ (4–25 μg/ml) producing hybridomas were similar. In order to assess if human Igλ rearrangement must precede mouse Igκ rearrangement or vice versa, endogenous and transgene rearrangements were analyzed. Southern blot hybridization of randomly picked human Igλ or mouse Igκ expressing hybridoma clones showed the following: from 11 human Igλ expressers, 7 had the mouse κ locus in germline configuration and only 1 clone had mouse Igκ rearranged, and from 19 mouse Igκ expressers, 17 had the human Igλ locus in germline configuration. The analysis of 8 more Igλ producers showed that in 2 the human Igλ locus was rearranged (data not shown). This result suggests that there is no locus activation bias and further emphasizes that the human λ translocus performs with similar efficiency than the endogenous locus.

Figure 4:
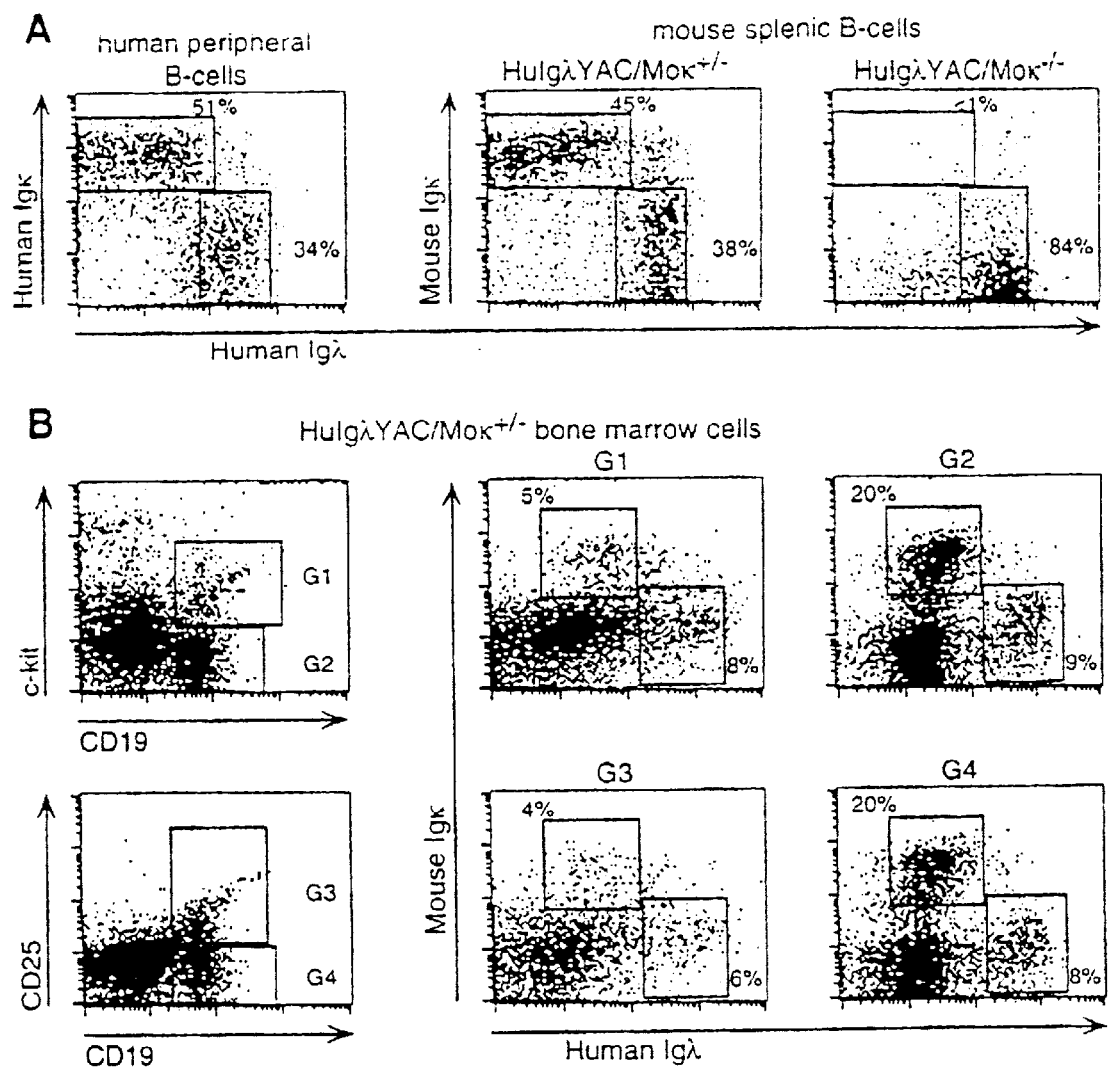
FIG. 4 depicts a flow cytometric analysis of light chain expression in the developing B-cell. (A) κ and λ light chain distribution of CD19$^+$ human peripheral lymphocytes and B220$^+$ mouse spleen cells from HuλYAC/Moκ$^{+/-}$ and HuλYAC/Moκ$^{-/-}$ mice. (B) Mouse Igκ and human Igλ light chain distribution in gated populations of CD19$^+$/c-kit$^+$ and CD19$^+$/CD25$^+$ bone marrow cells.

Hence the human λ locus is particularly well expressed in transgenic mice, even on a normal κ$^{+/+}$ or heterozygous κ$^{+/-}$ background, a result which was unexpected given the dominance of mouse κ over human κ in HuIgκ transgenic mice (64). FIG. 4 and the hybridoma results show that this has a developmental basis, with human λ often rearranging before mouse κ, which is also unexpected given the normal progression from κ to λ rearrangement for the endogenous mouse loci. The ability of the human 3' λ enhancer to function in the mouse background may be the reason that human λ and mouse κ levels are similar in HuIgλYAC+/κ$^{+/-}$ mice and that λ and κ light chain 3' enhancers compete at the pre B-cell stage to initiate light chain rearrangement.

The capacity of the human λ locus to produce an antibody repertoire is further documented in the V gene usage. V-J rearrangement was determined from spleen cells and Peyer's patch cells by PCR reactions, not biased by specific V gene primers. The results show that a substantial proportion of the Vλ genes on the translocus are being used with Vλ3-1 and Vλ3-10 being most frequently expressed. In DNA rearrangement, Jλ2 and Jλ3 were preferentially used and Jλ1 rarely, and as expected Jλ4, 5 and 6 were not utilized as they are adjacent to ψCs. Sequences obtained from RT-PCR products from FACS-sorted germinal centre PNA$^{+}$/B220$^{+}$ Peyer's patches revealed that somatic hypermutation is operative in HuIgλYAC mice (with somewhat more extensive changes in CDRs than in framework regions). Extensive variability due to N- or P-sequence additions, which is found in human but not mouse light chain sequences (25, 27, 28), was not observed.

Hybridomas and Human Monoclonal Antibodies from 5-Feature λ Mice

Figure 7:
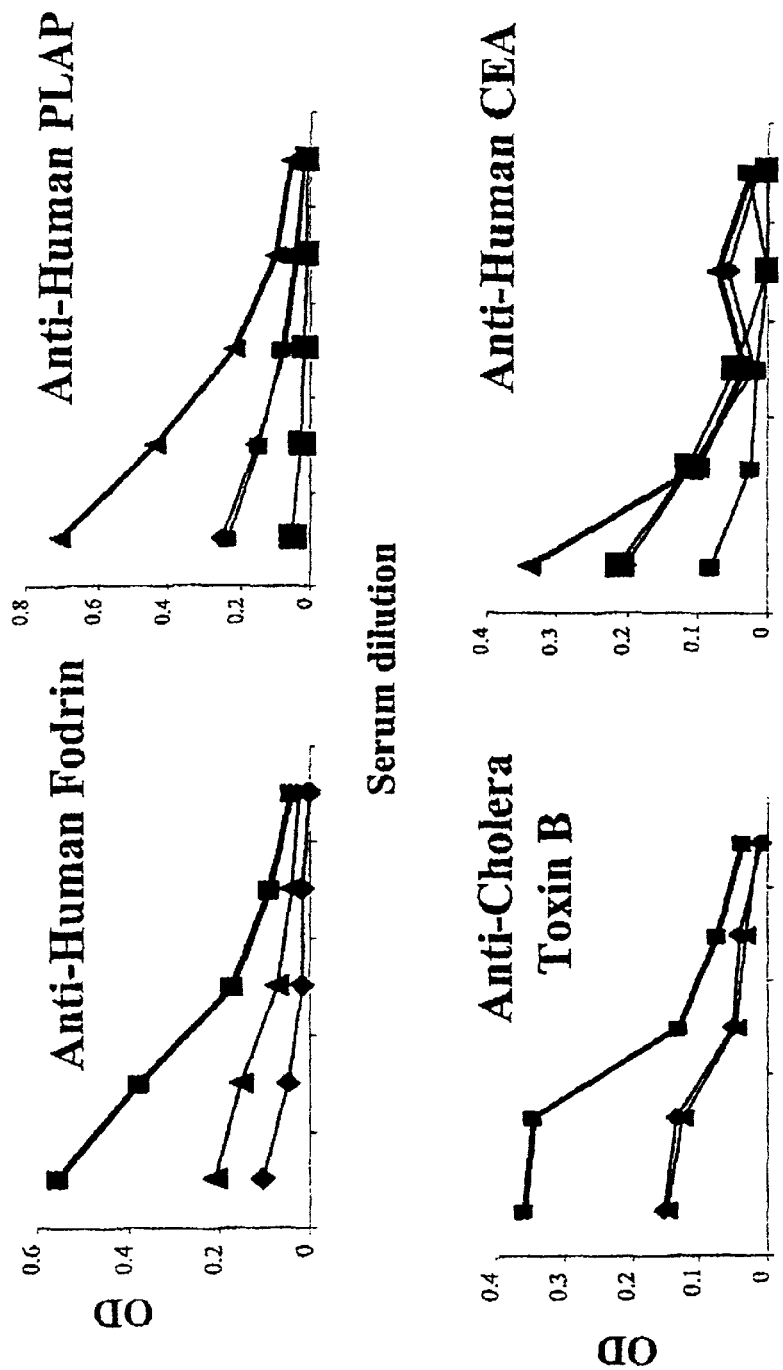
FIG. 7 depicts serum antibody titers in 5-feature transgenic mice following immunization with 4 antigens. The responses to human fodrin, human placental alkaline phosphatase (PLAP), the B subunit of cholera toxin and human carcinoembryonic antigen (CES) are shown, as measured by ELISA. In all cases the uppermost (bold) line is the response after 2 or 3 immunizations (background subtracted). ELISAs were developed with anti-human IgM antibodies linked to horseradish peroxidase.

Mice carrying the human λ translocus in the 5-feature genotype, i.e. together with human heavy and κ chain transloci and with endogenous heavy and κ chains silenced, were immunized with several human proteins, including fodrin, placental alkaline phosphatase (PLAP), carcinoembryonic antigen (CEA), the Fc fragment of human IgE, the steroid progesterone coupled to bovine serum albumin, and the bacterial protein cholera toxin subunit B. Periodic bleeds post-immunization showed good responses of IgM containing human λ and κ; mouse λ-containing Ig was barely detectable and was considerably lower than in 4-feature mice lacking human λ. The human antibody (IgM) responses of 5-feature mice to fodrin, PLAP, cholera toxin and CEA are shown in FIG. 7.

Hybridomas were produced from spleen cells of the immunized 5 feature mice and Ig producing clones were screened for human light chain production in order to determine the proportions of κ and λ. The number expressed in hybridomas is a good reflection of the expression of the light chains among B cells and in immune sera. The results summarized in Table 1 below show that in 7 fusions, there was a majority of human λ-producing hybridomas in 6, while in only one fusion was there a small preponderance of κ. The proportion of human λ ranged from a minimum of 75% of the human κ level to a maximum of 8 times greater than the κ level. In most cases (5/7) the number of human λ-producing hybridomas exceeded those making human κ by a factor of 4 fold or greater. This demonstrates the unexpectedly high expression of human λ in transgenic mice.

TABLE 1

| Antigen | Hybridomas | λ % | κ % | λ:κ |
| --- | --- | --- | --- | --- |
| Progest | 73 | 51 | 49 | 1.04 |
| Progest | 16 | 43 | 57 | 0.75 |
| IGF | 82 | 87 | 13 | 6.7 |
| IGF | 42 | 81 | 19 | 4.3 |
| IgE | 45 | 89 | 11 | 8.1 |
| IgE | 21 | 81 | 19 | 4.3 |
| IgE | 23 | 62 | 38 | 1.63 |

Frequency of occurrence of human λ and κ light chains among monoclonal immunoglobulins produced by hybridomas from immunized 5-feature translocus mice. The mice were immunized with the antigens shown in the far left column (Progest = progesterone-bovine serum albumin; IGF = insulin related growth factor; IgE = Fc fragment of human immunoglobulin E). Hybridomas were prepared and the number expressing λ or κ light chains were determined. The ratio of λ:κ is shown in the far right column.

Diversity of Rearrangements of the λ Light Chain Genes

Figure 2:
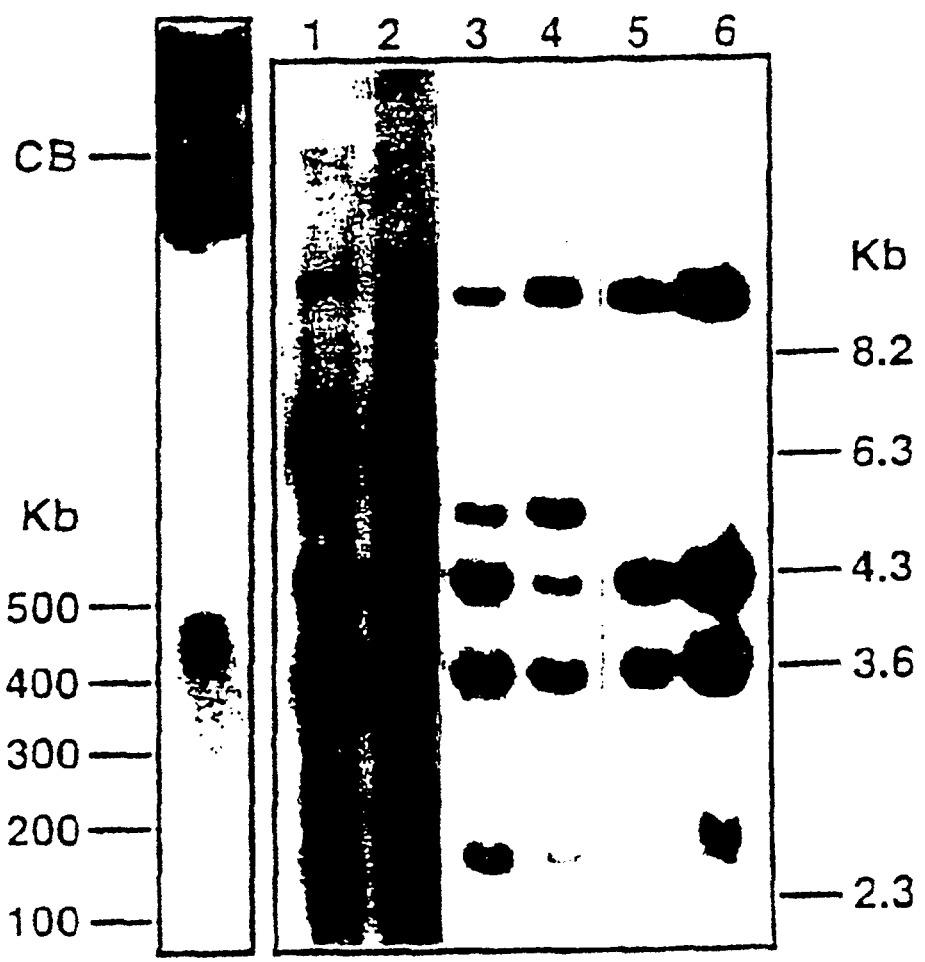
FIG. 2 depicts a Southern blot analysis of HuIgλYAC Integration. (Left) NotI digested testis DNA resolved on PFGE and hybridized with the Cλ2+3 probe. The same size band was obtained with the left arm probe (not shown). The majority of the hybridization signal remains in the compression band (CB) presumably due to protection of the NotI site by methylation. (Right) EcoRI/HindIII digests hybridized with the Cλ2+3 probe. Lane 1: HuIgλYAC ES cell DNA from a protoplast fusion clone; lane 2: normal ES cell DNA; lane 3: human genomic DNA (XZ); lane 4: human KB carcinoma (55) DNA; lane 5 and 6: tail DNA from 2 HuIgλYAC germline transmission mice. Note that the human DNA shows an additional 5.2 Kb band which represents an allelic variation (56).
Figure 5D:
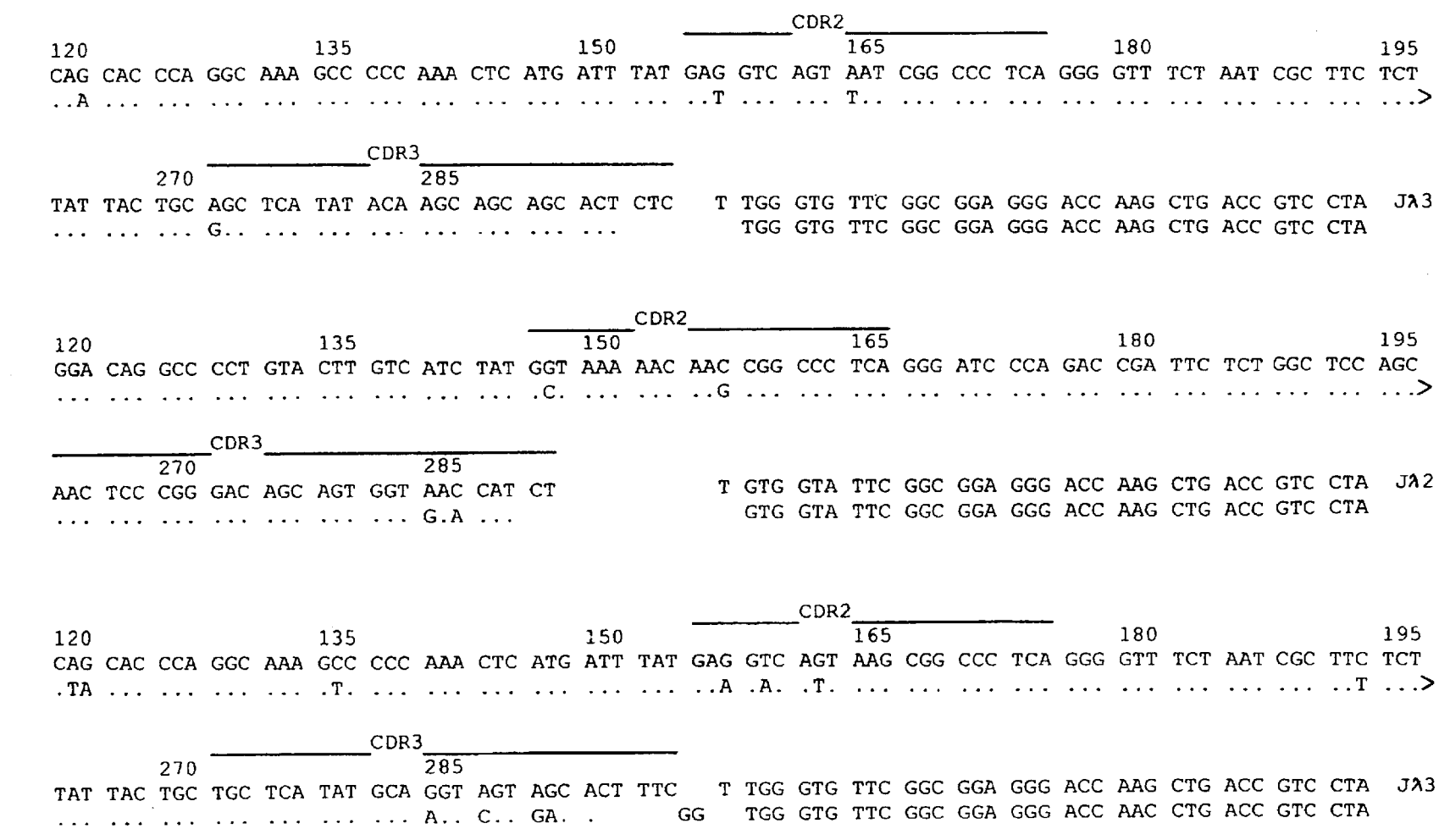

The utilization of individual Vλ genes is indicated by the triangles in FIG. 1, and shows that a substantial proportion of the Vλ genes on the translocus are being used in productive rearrangements, with Vλ 3-1 and Vλ 3-10 being most frequently expressed. In Vλ-Jλ rearrangements, Jλ 2 was preferentially used and Jλ 3 and J λ1 less frequently, and, as expected Jλ 4,5 and 6 were not utilized as they are adjacent to ψCs. Extensive variability due to N- or P-sequence additions, which is found in human but not mouse L chain sequences, was not observed. Sequences obtained by RT-PCR from FACS-sorted PP germinal centre B cells (B220+/PNA+) revealed that somatic hypermutation is operative in HuIgλ YAC mice (FIG. 5). Provided herein are unique 11Vλ-Jλ rearrangements with 2 or more changes in the V region, excluding CDR3, which may be affected by Vλ-Jλ recombination. The majority of mutations lead to amino acid replacements, but there was no preferential distribution in CDR1 and CDR2. Extensive somatic hypermutation of many rearranged human Igλ sequences were found, indicating that they were able to participate in normal immune responses.

Somatic Hypermutation in Human Igλ Rearrangements in 5-Feature λ Mice

Figure 6:
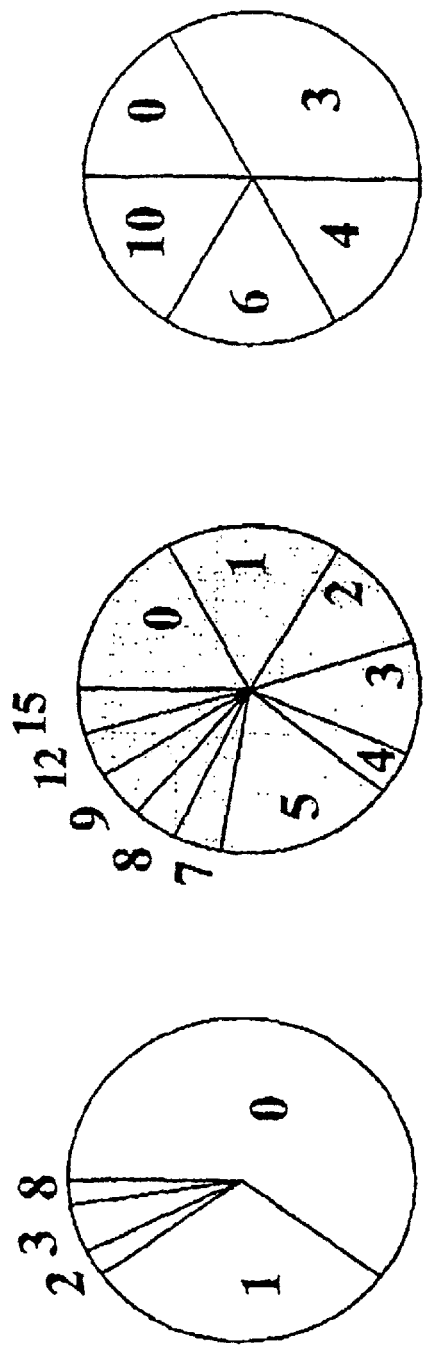
FIG. 6 illustrates the occurrence of somatic hypermutation in the H, κ and λ transloci of 5-feature mice after immunization. The number of mutations in individual sequenced chains are indicated in the pie chart which shows the frequency of their occurrence. 'Total analyzed' refers to the number of individual chains sequenced.

The occurrence of somatic mutations was determined by sequencing of rearrangements from B cells or hybridomas and comparison with germline sequences. The results shown in FIG. 6 show that the λ locus undergoes mutation with up to 10 point mutations being observed, with a comparable frequency to the κ locus and a considerably higher frequency than that seen in the IgH translocus. The 6 Igλ rearrangements were obtained by RT-PCR from a single 5 feature animal, and show a limited use of the V gene segments, with Vλ3-19 used in 5 sequences (FIG. 6). Given the high contribution to the B cell repertoire seen in FACS and serum analysis, it is likely that the rearrangement of the locus in the 5 feature mice is similar to what is seen in mice where the HuIgLambda YAC is in the presence of a functional mouse Igκ locus. Little or no 'N' insertion is found in the translocus-derived L chains, either in the 4 and 5 feature mice, or in mice with the HuIgKappa or HuIgLambda YAC in the presence of a functional mouse H chain locus. This would suggest that the L chain translocus rearranges at the same developmental stage as the endogenous L chains, at which time terminal deoxynucleotide transferase activity is reduced.

High Affinity Monoclonal Human Antibody from a 5-Feature λ Mouse.

Figure 8:
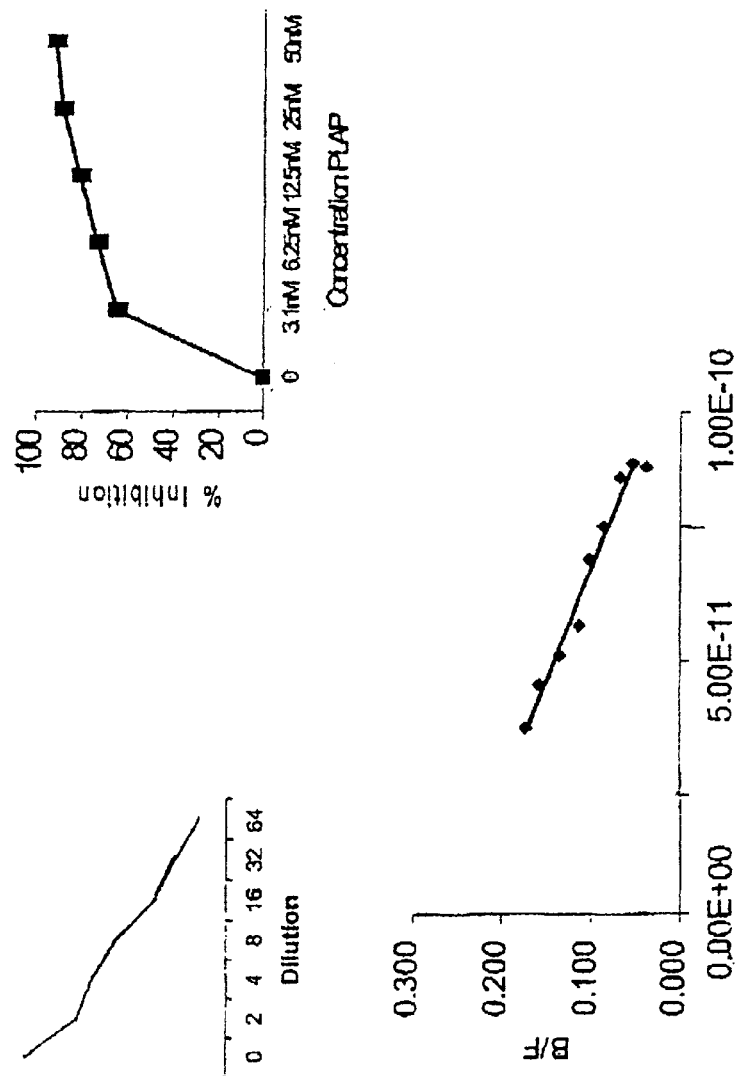
FIG. 8 shows the properties of a human λ-containing monoclonal antibody (7783.26) against human placental alkaline phosphatase (PLAP), produced from an immunized 5-feature mouse. (A) Titration of anti-PLAP from supernatant of an individual hybridoma clone of antibody 7783.26 against immobilized PLAP antigen in an ELISA assay, developed with anti-human λ antibodies linked to horseradish peroxidase. (B) Inhibition of binding of human anti-PLAP antibody 7783.26 by free PLAP. (C) Affinity determination of human anti-PLAP antibody 7783/26 by Scatchard plot after the method of Friguet et al (63). From the plot, the affinity (Ka) of this antibody was estimated to be $2 \times 10^9 M^{-1}$.

The occurrence of somatic hypermutation suggested that 5-feature mice would be capable of producing high affinity human antibodies, including those against human antigens of clinical importance. This was demonstrated for the IgM antibody 7783.26 against human placental alkaline phosphatase PLAP (FIG. 8). After cloning, the monoclonal antibody bound strongly to PLAP in ELISA, was sensitively inhibited by free PLAP (50% inhibition at about 2 nM) and from a Scatchard plot had an affinity of $2 \times 10^9$ $M^{-1}$. Hence, the mice are capable of giving rise to human antibodies with a high affinity which would be suitable for therapeutic purposes.

Efficient DNA rearrangement and high antibody expression levels are rarely achieved in transgenic mice carrying immunoglobulin regions in germline configuration on minigene constructs. Competition with the endogenous locus can be eliminated in Ig knock-out strains, where transgene expression is usually good (42). Poor transloci expression levels could be a result of the failure of human sequences in the mouse background, or alternatively the lack of locus specific control regions which are more likely to be included on larger transgenic regions (43, 44, 45). The latter is supported by the finding that HuIgλYAC mice express human Igλ and mouse Igκ at similar levels. The 410 Kb HuIgλYAC translocus accommodates V-gene region cluster A containing at least 15 functional Vλ genes (see FIG. 1). In man, cluster A is the main contributor to the λ antibody repertoire, with Vλ 2-14 (2a2) expressed most frequently at 27% in blood lymphocytes (23). Expression of Vλ2-14 in the transgenic mice was found, but the main contributors to λ light chain usage were 3-1, the Vλ gene most proximal to the C-J region, and 3-10, both of which are expressed at about 3% in man. Although the validity to draw conclusions about gene contribution is dependent on the numbers compared, from the 31 sequences obtained 11 showed were Vλ3-1 and 8 were Vλ3-10 which suggests that rearrangement or selection preferences are different in mouse and man. Sequence analysis revealed that there was very little further diversification by insertion of N or P nucleotides. In contrast, somatic hypermutation of some rearranged human Igλ sequences was found, indicating that they are able to participate in normal immune responses. Indeed mutation levels in B220[+]/PNA[+] PPs from HuIgλYAC translocus mice were similar to what has been reported for mouse light chains (46). In the mouse, unlike in humans, untemplated light chain diversification is essentially absent and it was believed that this is because deoxynucleotidyl transferase is no longer expressed at the stage of light chain rearrangement (28, 47). This concept has been challenged by the discovery that mouse light chain rearrangement can occur at the same time as $V_H$ to $DJ_H$ rearrangements (48). Indeed, these results also show light chain rearrangement at the pre B-I stage, with a substantial percentage of CD19[+] cells expressing human λ (see FIG. 4). Although the human λ translocus appears to be earlier activated than the κ locus in the mouse, rearranged human λ light chains did not accumulated much N region diversity as found in human peripheral B-cells (27).

In the different species, the ratio of λ and κ light chain expression varies considerably (1-3, 49, 50) and in the mouse the low λ light chain levels are believed to be a result of inefficient activation of the mouse λ locus during B-cell differentiation (reviewed in 6). The Igλ (~40%) and Igκ (~60%) ratio in humans is more balanced and suggests that both λ and κ play an equally important role in immune responses. This notion is supported by the finding that the mouse Vλ genes are most similar to the less frequently used human Vλ gene families, while no genes comparable to the major contributors to the human Vλ repertoire are present in mice (40). With the HuIgλYAC, these Vλ genes are available, and are able to make a significant contribution to the antibody repertoire, and the bias towards Vκ gene utilization is removed.

Comparison of size and complexity of light chain loci between different species suggests that larger loci with many more V genes may contribute much more efficiently to the antibody repertoire (6, 51). Recently, this question was addressed in transgenic mice by the introduction of different size human κ light chain loci (45). The result showed that the size of the V gene cluster and the V gene numbers present are not relevant to achieving high translocus expression levels. It is possible, however, that a presently undefined region with cis-controlled regulatory sequences may be crucial in determining expressibility and subsequently light chain choice. That the HuIg1YAC$^+$/κ$^{+/-}$ mice do not exhibit a bias in the selection of light chain locus for expression is shown by the absence of rearrangement of the non-expressed locus in hybridoma cells. This supports the model that λ and κ rearrangements are indeed independent (52) and that poor Igλ expression levels in mice may be the result of an inefficient recombination signal (53). A possible signal that initiates light chain recombination has been identified in gene targeting experiments where the 3'κ enhancer has been deleted (19). The κ:λ ratio was essentially equal in mice where the 3'Eκ had been deleted or replaced by neo (down to 1:1 and not 20:1 as in normal mice). In addition, the κ locus was largely in germline configuration in λ expressing cells, a result also seen in the HuIgλYAC$^+$/κ$^{+/-}$ mice. Taken together, the results suggest that the ability of the human 3' λ enhancer to function in the mouse background may be the reason that human λ and mouse κ levels are similar in HuIgλYAC$^+$/κ$^{+/-}$ mice and that λ and κ light chain 3' enhancers compete at the pre B-cell stage to initiate light chain rearrangement.

REFERENCES

The following are hereby incorporated by reference.

1. Hood, L., Gray, W. R., Sanders, B. G. and Dreyer, W. Y. (1967) *Cold Spring Harbor Symp. Quant. Biol.* 32:133–46.
2. McIntire, K. R. and Rouse, A. M. (1970) *Fed. Proc.* 19: 704.
3. Arun, S. S., Breuer, W. and Hermanns, W. (1996) *Zentralbl. Veterinarmed. A.* 43: 573–76.
4. Hieter, P. A., Korsmeyer, S. J., Waldmann, T. A and Leder, P. (1981) *Nature* 290: 368–72.
5. Coleclough, C., Perry, R. P., Karjalainen, K. and Weigert, M. (1981) *Nature* 290: 372–78.
6. Selsing, E. and Daitch, L. E. (1995) Immunoglobulin λ genes. In *Immunoglobulin Genes*, 2nd Ed., eds. T. Honjo and F. W. Alt, Rabbitts. Academic Press: 193–203.
7. Berg, J., McDowell, M., Jack, H. M. and Wabl, M. (1990) *Dev. Immunol.* 1, 53–57.
8. Abken, H. and Bützler, C (1991) *Immunol.* 74: 709–713.
9. Takemori, T. and Rajewsky, K. (1981) *Eur. J. Immunol.* 11: 618–25.
10. McGuire, K. L. and Vitetta, E. S. (1981) *J. Immunol.* 127: 1670–73.
11. Kessler, S., Kim, K. J. and Scher, I. (1981) *J. Immunol.* 127: 1674–78.
12. Lejeune, J. M., Briles, D. E., Lawton, A. R. and Kearney, J. F. (1982) *J. Immunol.* 129: 673–677.
13. Rolink, A., Streb, M. and Melchers, F. (1991) *Eur. J. Immunol.* 21, 2895–98.
14. Osmond, D. J., Rolink, A. and Melchers, F (1998) *Immunol. Today* 19, 65–68.
15. Zou, Y. R., Takeda, S. and Rajewsky, K. (1993) *EMBO J.* 12: 811–20.
16. Arakawa, H., Shimizu, T. and Takeda, S. (1996). *Int. Immunol.* 8: 91–99.
17. Glozak, M. and Blomberg, B. B. (1996) *Mol. Immunol.,* 33: 427–38.
18. Asenbauer, H and Klobeck, H. G. (1996) *Eur. J. Immunol.* 26: 142–50.
19. Gorman, J. R., van der Stoep, N., Monroe, R., Cogne, M., Davidson, L. and Alt, F. W. (1996) *Immunity* 5, 241–52.
20. Frippiat, J.-P., Williams, S. C., Tomlinson, I. M., Cook, G. P., Cherif, D., Le Paslier, D., Collins, J. E., Dunham, I., Winter, G. and Lefranc, M.-P (1995) *Hum. Mol. Genet.* 4: 983–91.
21. Kawasaki, K., Minoshimna, S., Nakato, E., Shibuya, K., Shintani, A., Schmeits, J. L., Wang, J. and Shimizu, N. (1997) *Genome Res.* 7: 260–61.
22. Giudicelli, V., Chaume, D., Bodmer, J., Muller, W., Busin, C., Marsh, S., Bontrop, R., Marc, L., Malik, A. and Lefranc, M.-P. (1997) *Nucl. Acids Res.,* 25: 206–11.
23. Ignatovich, O., Tomlinson, I. M., Jones, P. T. and Winter, G., (1997) *J. Mol. Biol.* 268: 69–77.
24. Combriato, G. and Klobeck, H.-G. (1991) *Eur. J. Immunol.,* 21: 1513–22.
25. Foster, S. J., Brezinschek, H.-P., Brezinschek, R. I and Lipsky, P. E. (1997) *Clin. Invest.,* 99, 1614–27.
26. Ignatovich, O. The creation of diversity in the human immunoglobulin Vλ repertoire. PhD thesis, University of Cambridge, 1998.
27. Bridges, S. L., Lee, S. K., Johnson, M. L., Lavelle, J. C., Fowler, P. G., Koopman, W. J. and Schroeder, (1995) *J. Clin. Invest.,* 96, 831–41.
28. Victor, K. D., Vu, K. anf Feeney, A. J. (1994) *J. Immunol.,* 152: 3467–75.
29. Popov, A V., Büitzler, C., Frippiat, J-P., Lefranc, M-P., Brüggemann, M. (1996). *Gene* 177: 195–201.
30. Davies, N. P., Popov, A. V., Zou, X. and Brüggemann, M. (1996). Human antibody repertoires in transgenic mice: Manipulation and transfer of YACs. *Antibody Engineering: A Practical Approach,* eds. J. McCafferty, H. R. Hoogenboom and D. J. Chiswell, IRL, Oxford: 59–76.
31. Hogan, B., Beddington, R., Costantini, F. and Lacy E. (1994) Manipulating the Mouse Embryo: A Laboratory Manual. *Cold Spring Harbor Laboratory Press.*
32. Zou, X., Xian, J., Popov, A. V., Rosewell, I. R, Müller, M and Brüggemann, M (1995) *Eur J. Immunol.* 25: 2154–62.
33. Wurst, W. and Joyner, A. L. Production of targeted embryonic stem cell DNA. In: *Gene targeting,* ed. A. L. Joyner. IRL Press, Oxford, 1993: 33–61.
34. Herrmann B. G., Barlow D. P., and Lehrach, H., (1987) *Cell* 48: 813–25.
35. Galfré, G. and Milstein, C. (1981) Methods Enzymol, 73:3–46.
36. Tijssen, P. Practice and theory of enzyme immunoassays. *Laboratory techniques in biochemistry and molecular biology.* Vol. 15. Burdon, R. H. and Knippenberg, P. H. (eds.) Elsevier, 1985.
37. Chomczynski, P. and Sacchi, N. (1987) *Anal. Biochem.* 162: 156–159.
38. Frohman, M. A., Dush, M. K. and Martin, G. R. (1988) *Proc. Natl. Acad. Sci, USA* 85: 8998–9002.
39. *Current protocols in molecular biology* (1995) eds. Ausubel, F. M., Brent, R., Kingston, R. E., Moore, D. D., Seidman, J. G., Struhl, K., Smith, J. A. Massachusetts General Hospital, Boston, Mass.: Harvard Medical School, Boston, Mass.; University of Alabama, Birmingham, Ala.; Wiley & Sons, USA.
40. Williams, S. C., Frippiat, J.-P., Tomlinson, I. M., Ignatovich, O., Lefranc, M.-P. and Winter, G. (1996) *J. Mol. Biol.* 264: 220–32.
41. Chen, J., Trounstine, M., Kurahara, C., Young, F., Kuo, C.-C., Xu, Y., Loring, J. F., Alt, F. W. and Huszar, (1997) D. *EMBO J.* 12: 821–30.
42. Brüggemann, M. and Neuberger, M. S. (1996) *Immunol. Today,* 17: 391–97.
43. Green, L. L. and Jakobovits, A. (1998) *J. Exptl. Med.* 188: 483–95.
44. Zou, X., Xian, J., Davies, N. P., Popov, A. V. and Brüggemann, M. (1996) *FASEB J.,* 10: 1227–32.
45. Xian, J., Zou, X., Popov, A. V., Mundt, C. A., Miller, N., Williams, G. T., Davies, S. L., Neuberger, M. S. and Brüggemann, M. (1998) *Transgenics* 2: 333–43.
46. Gonzalez-Fernandez, A., Gupta, S. K., Pannell, R., Neuberger, M. S. and Milstein, C. (1994) *Proc. Natl. Acad. Sci. USA* 91: 12614–18.
47. Li, Y-S., Hayakawa, K. and Hardy, R. R. (1993) *J. Exp. Med.* 178: 951–60.
48. Hardy, R. R., Carmack, C. E., Shinton, S. A., Kemp, J. D. and Hayakawa, K. (1991) *J. Exp. Med.,* 173, 1213.
49. Saitta, M., Iavarone A., Cappello, N., Bergami, M R., Fiorucci, G. C. and Aguzzi, F. (1992) *Clin Chem.* 38: 2454–57.
50. Hood, L., Eichmann, H., Lackland, H., Krause, R. M and Ohms, J. J. (1970) *Nature* 228: 1040.
51. Lansford, R., Okada, A., Chen, J., Oltz, E. M., Blackwell, T. K., Alt, F. W. and Rathburn, G. (1996) Mechanisms and control of immunoglobulin gene rearrangement. In *Molecular Immunology,* B. D. Hames and D. M. Glover, eds. (New York: IRL Press): 1–100.
52. Nadel, B., Cazenave, P.-A. and Sanchez, P. (1990) *EMBO J.,* 9: 435–40.
53. Arakawa, H., Shimizu, T. and Takeda, S. (1996). *Int. Immunol.* 8: 91–99.
54. Giudicelli, V., Chaume, D., Bodmer, J., Muller, W., Busin, C., Marsh, S., Bontrop, R., Marc, L., Malik, A. and Lefranc, M.-P. (1997) *Nucl. Acids Res.* 25: 206–11.
55. Eagle, H. (1955) *Proc. Soc. Exptl. Biol. Med.* 89: 362–64.
56. Taub, R. A., Hollis, G. F., Hieter, P. A., Korsmeyer, S., Waldmann, T. A. and Leder, P. (1983) *Nature (London)* 304: 172–74.
57. Kitamura, D., Roes, J., Kahn, R., and Rajewsky, K, (1991) *Nature* 350: 423.
58. PCT/GB89/01207.
59. Bruggemann and Neuberger (1996) *Immunology Today* 17: 391–97.
60. Bruggemann and Taussig (1997) *Curr. Opinion Biotech.* 8: 455–58.
61. Mendez et al. (1997) *Nat. Genet.* 15: 146–56.
62. Fishwild et al. (1996) *Nat. Biotechnol.* 14: 845–51.
63. Friguet et al., (1985) *J. Immunol. Methods* 77: 305–19.
64. Xian et al. (1998) *Transgenics* 2: 333–44.
65. Nicholson, I. et al. (1999) *J. Immunology* 163: 6898–6906.

This application claims priority to GB 9823930.4, filed Nov. 3, 1998, the entirety of which is hereby incorporated by reference.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A transgenic mouse comprising in its genome a yeast artificial chromosome (YAC), wherein the YAC contains at least a majority of the human Ig Vλ genes of cluster A and all the human Ig Jλ-Cλ segments in germline configuration, wherein the proportion of the κ and λ light chains expressed by said transgenic mouse resembles that found in humans, and exhibits relative proportions of <60% κ light chains and >40% λ light chains, wherein at least one endogenous κ light chain locus of the transgenic mouse is not disrupted.

2. The transgenic mouse according to claim 1, wherein the YAC is about 410 Kb, and wherein the YAC containing human Ig segments shows high expression and is able to compete with the endogenous mouse κ locus.

3. The transgenic mouse according to claim 1, wherein one of the endogenous Igκ loci of the mouse is disrupted, and wherein the YAC containing human Ig segments shows high expression.

4. The transgenic mouse according to claim 1, comprising a 380 Kb region of the human immunoglobulin (Ig) λ light (L) chain locus in germline configuration wherein the 380 Kb region resides on a yeast artificial chromosome (YAC) that accommodates the most proximal V (variable gene) λ cluster, wherein the 380 Kb regions has 15 Vλ genes and all J λ-C λ segments with the 3' region, wherein the 3' region includes a downstream enhancer.

5. The transgenic mouse according to claim 1, wherein the mouse includes a HuIgλ YAC that accommodates a 380 Kb region of the human λ light chain locus in authentic configuration with all Vλ genes of cluster A, the Jλ-Cλ segments and the 3' enhancer.

6. The transgenic mouse according to claim 5, wherein the HuIgλ YAC is shown in FIG. 1.

7. A method for producing a transgenic mouse according to claim 1, comprising:
    (a) introducing a HuIgλ YAC into murine embryonic stem cells, wherein the HuIgλ YAC accommodates a 380 Kb region of the human λ light chain locus in germline configuration with all Vλ genes of cluster A, the Jλ-Cλ segments, and a downstream enhancer at the 3' region; and
    (b) deriving a transgenic mouse from the cells of step (a) by blastocyte injection to form a chimeric animal and then breeding the chimeric mouse to obtain a transgenic mouse.

8. The method of claim 7, wherein the HuIgλ YAC is about 410 Kb.

9. The method according to claim 7, wherein two copies of the neomycin resistance gene (NEO$^r$) are site-specifically integrated into the ampicillin gene on the left (centromeric) YAC arm in order to permit selection.

10. The method according to claim 7, wherein YAC-containing yeast cells are fused with HM-1 embryonic stem (ES) cells and G418 resistance colonies are picked and analysed 2–3 weeks after protoplast fusion.

11. The method according to claim 7, wherein ES cells containing a complete HuIgλ YAC copy are used for blastocyte injection to produce a chimeric animal.

12. The method according to claim 11, wherein breeding of a chimeric animal with a Balb/c mouse results in germline transmission.

13. The method according to claim 12, wherein the germline transmission establishes lines of transgenic mice, wherein at least one endogenous κ light chain locus of the transgenic mouse is not disrupted.

14. A transgenic mouse comprising in its genome a yeast artificial chromosome (YAC), wherein the YAC contains at least a majority of the human Ig Vλ genes of cluster A and all the human Ig Jλ-Cλ segments in germline configuration, and expressing human λ light chain locus genes and endogenous κ light chain locus genes, wherein the expression of the human λ locus is equal to or greater than that of the endogenous κ light chain locus, and wherein at least one endogenous κ light chain locus of the transgenic mouse is not disrupted.

15. The transgenic mouse according to claim 14, wherein the mouse further comprises a human κ light chain locus and wherein expression of the human λ light chain locus is equal to or greater than that of the human κ light chain locus.

16. The transgenic mouse according to claim 14, wherein the λ locus has been bred to homozygosity.

17. The transgenic mouse according to claim 14, wherein the rearranged variable genes in the λ locus are subject to somatic hypermutation.

18. The transgenic mouse according to claim 14, wherein the mouse comprises a yeast artificial chromosome (YAC) of greater than 100 Kb which contains at least a majority of the human Vλ genes proximal to the Jλ-Cλ cluster in germline configuration.

19. The transgenic mouse according to claim 18, wherein the YAC includes a 380 Kb region of the human Igλ locus in authentic configuration with at least a majority of the Vλ genes of cluster A, Jλ-Cλ segments and a 3' enhancer.

20. The transgenic mouse according to claim 18, wherein the transgenic mouse comprises variable, joining and constant genes of the human λ light chain locus as a transgenic locus on a YAC, wherein B cells of said mouse rearranges said λ light chain genes and the mouse expresses serum immunoglobulins containing human λ light chains.

21. The transgenic mouse according to claim 18, wherein the λ locus is rearranged with similar efficiency as endogenous mouse κ and at the same time as or before the endogenous κ locus.

22. The transgenic mouse according to claim 18, wherein one of the the endogenous κ loci is silenced, and the mouse expresses serum immunoglobulins containing human λ light chains.

23. The transgenic mouse according to claim 18, further comprising human heavy chain genes as a second transgenic locus integrated on a separate YAC, wherein the mouse expresses serum immunoglobulin molecules containing combinations of human heavy and λ light chains.

24. The transgenic mouse according to claim 23, wherein the second transgenic locus carries a diversity of human heavy chain constant region genes and includes $\mu$, $\delta$ and y genes.

25. The transgenic mouse according to claim 24, wherein the heavy chain transgenic locus carries a diversity of human heavy chain constant region genes and includes $\mu$, $\delta$ and y genes, wherein the heavy chain constant regions genes are in authentic germline configuration.

26. The transgenic mouse according to claim 18, further comprising human κ light chain genes as a second transgenic light chain locus integrated on a separate YAC, wherein the mouse expresses serum immunoglobulin molecules containing human κ and λ light chains.

27. The transgenic mouse according to claim 18, further comprising human heavy chain genes as a second transgenic locus and human κ light chain genes as a third transgenic locus, wherein the mouse expresses serum immunoglobulin molecules containing human heavy chains in combination with at least one of human κ or λ light chains.

28. The transgenic mouse according to claim 18, wherein expression of the endogenous mouse heavy and/or light chain loci are prevented and the transgenic mouse expresses serum immunoglobulin containing human heavy and/or light chains, wherein at least one endogenous κ light chain locus of the transgenic mouse is not disrupted, and wherein the transgenic mouse is deficient in production of mouse immunoglobulin.

* * * * *

SEQUENCE LISTING

```
<160> NUMBER OF SEQ ID NOS: 23

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aattctaaaa ctacaaactg ccccccccd                                         29

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aattctaaaa ctacaaactg c                                                 21

<210> SEQ ID NO 3
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcccgggta gaagtcac                                                   18

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aattcgtgtg gccttgttgg ct                                              22

<210> SEQ ID NO 5
<211> LENGTH: 234
<212> TYPE: DNA
<213> ORGANISM: Homo sapiens

<400> SEQUENCE: 5
gccagcatca cctgctctgg agataaattg ggggataaat atgcttgctg gtatcagcag     60
aagccaggcc agtcccctgt gctggtcatc tatcaagata gcaagcggcc ctcagggatc    120
cctgagcgat tctctggctc caactctggg aacacagcca ctctgaccat cagcgggacc    180
caggctatgg atgaggctga ctattactgt caggcgtggg acagcagcac tgca          234

<210> SEQ ID NO 6
<211> LENGTH: 231
<212> TYPE: DNA
<213> ORGANISM: Homo sapiens

<400> SEQUENCE: 6
gccaacatca cctgttctgg agataaattg ggggataaat atgcttgctg gtatcagcag     60
aagccaggcc agtcccctat tctgatcatc tatcaagata acaggcggcc ctcagggatc    120
cctgagcgat tctctggctc caactctggg aacacagcca ctctgaccat cagcgggacc    180
caggctatgg atgaggctga ctattattgt caggcgtggg accgcagcac t             231

<210> SEQ ID NO 7
<211> LENGTH: 37
<212> TYPE: DNA
<213> ORGANISM: Homo sapiens

<400> SEQUENCE: 7
ttgggtgttc ggcggaggga ccaagctgac cgtccta                              37

<210> SEQ ID NO 8
<211> LENGTH: 36
<212> TYPE: DNA
<213> ORGANISM: Homo sapiens

<400> SEQUENCE: 8
tgggtattcg gcggagggac ctacctgacc gtcctg                               36

<210> SEQ ID NO 9
<211> LENGTH: 232
<212> TYPE: DNA
```

<210> SEQ ID NO 9
<211> LENGTH: 232
<212> TYPE: DNA
<213> ORGANISM: Homo sapiens

<400> SEQUENCE: 9

```
gccagcatca cctgctcgag agataaattg ggggaaacat atgtttcctg gtatcggcag      60
aagccaggcc agtcccctgt gctgctcatc tatcaagata ccaagcgacc ctcagggatc     120
cctgagcgat tctctggctc caactctggg aacacagccg ctctgaccat caccgggacc     180
caggctttgg atgaggctga ctattactgt caggcgtggg acagcgccac tg             232
```

<210> SEQ ID NO 10
<211> LENGTH: 37
<212> TYPE: DNA
<213> ORGANISM: Homo sapiens

<400> SEQUENCE: 10

```
tgtggtattc ggcggaggga ccaagctgac cgtccta                               37
```

<210> SEQ ID NO 11
<211> LENGTH: 35
<212> TYPE: DNA
<213> ORGANISM: Homo sapiens

<400> SEQUENCE: 11

```
tggttttcgg cggagggacc aaactgacca tccta                                 35
```

<210> SEQ ID NO 12
<211> LENGTH: 239
<212> TYPE: DNA
<213> ORGANISM: Homo sapiens

<400> SEQUENCE: 12

```
gccaggatca cctgctctgg agatgcattg ccaaaaaaat atgcttattg gtaccagcag      60
aagtcaggcc aggcccctgt gctggtcatc tatgaggaca gcaaacgacc ctccgggatc     120
cctgagagat tctctggctc cagctcaggg acaatggcca ccttgactat cagtggggcc     180
caggtggagg atgaagctga ctactactgt tactcaacag acagcagtgg taatcatag     239
```

<210> SEQ ID NO 13
<211> LENGTH: 239
<212> TYPE: DNA
<213> ORGANISM: Homo sapiens

<400> SEQUENCE: 13

```
gccaggatca cctgctctgg agatgcattg ccaaaaaaat atgcttattg gtaccagcag      60
aagtcaggcc aggcccctgt gctggtcatc tctgaggaca gcaaacgacc ctccgggatc     120
cctgagagaa tctctggctc cagctcaggg acaatggcca ccttgactat cagtggggcc     180
caggtggaag atgaagctga ctactactgt tactcaacag acagcagtag tactcatag     239
```

<210> SEQ ID NO 14
<211> LENGTH: 34
<212> TYPE: DNA
<213> ORGANISM: Homo sapiens

<400> SEQUENCE: 14

```
ggtgttcggc ggagggacca agctgaccgt ccta                                  34
```

<210> SEQ ID NO 15
<211> LENGTH: 246
<212> TYPE: DNA
<213> ORGANISM: Homo sapiens

<400> SEQUENCE: 15

| | | | | |
|---|---|---|---|---|
| atcaccatct | cctgcactgg | aaccagcagt | gacgttggtg | gttataacta tgtctcctgg | 60 |
| taccaacagc | acccaggcaa | agcccccaaa | ctcatgattt | atgaggtcag taatcggccc | 120 |
| tcagggtttt | ctaatcgctt | ctctggctcc | aagtctggca | acacggcctc cctgaccatc | 180 |
| tctgggctcc | aggctgagga | cgaggctgat | tattactgca | gctcatatac aagcagcagc | 240 |
| actctc | | | | | 246 |

<210> SEQ ID NO 16
<211> LENGTH: 243
<212> TYPE: DNA
<213> ORGANISM: Homo sapiens

<400> SEQUENCE: 16

| | | | | |
|---|---|---|---|---|
| atcaccatct | cctgcactgg | aaccagcagt | gacgttggtg | gttctaactt tgtctcctgg | 60 |
| taccaacaac | acccaggcaa | agcccccaaa | ctcatgattt | atgatgtcag ttatcggccc | 120 |
| tcagggtttt | ctaatcgctt | ctctggctcc | aagtctggca | acacggcctc cctgaccatc | 180 |
| tctgggctcc | aggctgagga | cgaggctgat | tattactgcg | gctcatatac aagcagcagc | 240 |
| act | | | | | 243 |

<210> SEQ ID NO 17
<211> LENGTH: 36
<212> TYPE: DNA
<213> ORGANISM: Homo sapiens

<400> SEQUENCE: 17

| | | |
|---|---|---|
| tgggtgttcg | gcggagggac | caagctgacc gtccta | 36 |

<210> SEQ ID NO 18
<211> LENGTH: 239
<212> TYPE: DNA
<213> ORGANISM: Homo sapiens

<400> SEQUENCE: 18

| | | | | |
|---|---|---|---|---|
| gtcaggatca | catgccaagg | agacagcctc | agaagctatt | atgcaagctg gtaccagcag | 60 |
| aagccaggac | aggcccctgt | acttgtcatc | tatggtaaaa | acaaccggcc ctcagggatc | 120 |
| ccagaccgat | tctctggctc | cagctcagga | aacacagctt | ccttgaccat cactggggct | 180 |
| caggcggaag | atgaggctga | ctattactgt | aactcccggg | acagcagtgg taaccatct | 239 |

<210> SEQ ID NO 19
<211> LENGTH: 237
<212> TYPE: DNA
<213> ORGANISM: Homo sapiens

<400> SEQUENCE: 19

| | | | | |
|---|---|---|---|---|
| gtcaggatca | catgccaagg | agacagcctc | agaagctatt | atgcaagctg gttccagcag | 60 |
| aagccaggac | aggcccctgt | acttgtcatc | tatgctaaaa | acaagcggcc ctcagggatc | 120 |
| ccagaccgat | tctctggctc | cagctcagga | aacacagctt | ccttgaccat cactgggact | 180 |
| caggcggaag | atgaggctga | ctattactgt | aactcccggg | acagcagtgg tgaacat | 237 |

<210> SEQ ID NO 20
<211> LENGTH: 36
<212> TYPE: DNA
<213> ORGANISM: Homo sapiens -continued

```
<400> SEQUENCE: 20
gtggtattcg gcggagggac caagctgacc gtccta                                36

<210> SEQ ID NO 21
<211> LENGTH: 246
<212> TYPE: DNA
<213> ORGANISM: Homo sapiens

<400> SEQUENCE: 21
atcaccatct cctgcactgg aaccagcagt gatgttggga gttataacct tgtctcctgg      60
taccaacagc acccaggcaa agcccccaaa ctcatgattt atgaggtcag taagcggccc     120
tcagggsttt ctaatcgctt ctctggctcc aagtctggca acacggcctc cctgacaatc    180
tctgggctcc aggctgagga cgaggctgat tattactgct gctcatatgc aggtagtagc    240
actttc                                                                246

<210> SEQ ID NO 22
<211> LENGTH: 241
<212> TYPE: DNA
<213> ORGANISM: Homo sapiens

<400> SEQUENCE: 22
atcaccatct cctgcactgg aaccagcggt gatgttggga gttataactt tgtctcctgg     60
taccaactac acccaggcaa agtccccaaa ctcatgattt atgaagacat taagcggccc    120
tcagggsttt ctaatcgctt ttctgcctcc aagtctggca acacggcctc cctgacaatc    180
tctgggctcc aggctgagga cgaggctgat tattactgct gctcatatgc aagtcgtgac    240
a                                                                    241

<210> SEQ ID NO 23
<211> LENGTH: 38
<212> TYPE: DNA
<213> ORGANISM: Homo sapiens

<400> SEQUENCE: 23
ggtgggtgtt cggcggaggg accaacctga ccgtccta                              38
```